US009457057B2

(12) United States Patent
Tompkins et al.

(10) Patent No.: US 9,457,057 B2
(45) Date of Patent: Oct. 4, 2016

(54) METHODS FOR THE PREVENTION AND TREATMENT OF BURN INJURIES AND SECONDARY COMPLICATIONS

(71) Applicant: The General Hospital Corporation, Boston, MA (US)

(72) Inventors: Ronald G. Tompkins, Boston, MA (US); A. Aria Tzika, Jamaica Plain, MA (US); Yong-Ming Yu, Cambridge, MA (US); Laurence Rahme, Jamaica Plain, MA (US); Jeevendra A. Martyn, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/061,370

(22) Filed: Oct. 23, 2013

(65) Prior Publication Data

US 2014/0288012 A1    Sep. 25, 2014

Related U.S. Application Data

(63) Continuation of application No. 12/727,647, filed on Mar. 19, 2010, now abandoned.

(60) Provisional application No. 61/162,060, filed on Mar. 20, 2009, provisional application No. 61/249,658, filed on Oct. 8, 2009, provisional application No. 61/258,533, filed on Nov. 5, 2009, provisional application No. 61/259,349, filed on Nov. 9, 2009.

(51) Int. Cl.
*A61K 38/07* (2006.01)

(52) U.S. Cl.
CPC .................................... *A61K 38/07* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 5,312,899 | A | 5/1994 | Schiller |
| 5,602,100 | A | 2/1997 | Brown et al. |
| 5,652,122 | A | 7/1997 | Frankel et al. |
| 5,674,534 | A | 10/1997 | Zale et al. |
| 5,716,644 | A | 2/1998 | Zale et al. |
| 5,885,958 | A | 3/1999 | Zadina et al. |
| 5,993,848 | A | 11/1999 | Suzuki et al. |
| 5,994,372 | A | 11/1999 | Yaksh |
| 6,221,355 | B1 | 4/2001 | Dowdy |
| 6,268,398 | B1 | 7/2001 | Ghosh et al. |
| 6,468,798 | B1 | 10/2002 | Debs et al. |
| 6,503,713 | B1 | 1/2003 | Rana |
| 6,521,271 | B1 | 2/2003 | Phan |
| 6,703,483 | B1 | 3/2004 | Schiller |
| 6,759,520 | B1 | 7/2004 | Carr et al. |
| 6,900,178 | B2 | 5/2005 | Oeltgen et al. |
| 7,498,297 | B2 | 3/2009 | Szeto et al. |
| 7,541,340 | B2 | 6/2009 | Szeto et al. |
| 7,550,439 | B2 | 6/2009 | Szeto |
| 7,576,061 | B2 | 8/2009 | Szeto et al. |
| 7,704,954 | B2 | 4/2010 | Szeto et al. |
| 7,718,620 | B2 | 5/2010 | Szeto et al. |
| 7,732,398 | B2 | 6/2010 | Szeto et al. |
| 2004/0248808 | A1* | 12/2004 | Szeto et al. ..................... 514/15 |
| 2005/0096333 | A1 | 5/2005 | Dugar et al. |
| 2005/0158373 | A1 | 7/2005 | Szeto et al. |
| 2005/0192215 | A1 | 9/2005 | Ghosh et al. |
| 2006/0084606 | A1 | 4/2006 | Szeto |
| 2007/0015711 | A1 | 1/2007 | Szeto |
| 2007/0027070 | A1 | 2/2007 | Szeto et al. |
| 2007/0027087 | A1 | 2/2007 | Szeto et al. |
| 2007/0093969 | A1 | 4/2007 | Mendrick et al. |
| 2007/0129306 | A1 | 6/2007 | Szeto et al. |
| 2007/0259377 | A1 | 11/2007 | Urdea et al. |
| 2008/0014604 | A1 | 1/2008 | Devarajan et al. |
| 2008/0027082 | A1 | 1/2008 | Hocher et al. |
| 2009/0221514 | A1 | 9/2009 | Szeto et al. |
| 2009/0253641 | A1 | 10/2009 | Neufer et al. |
| 2009/0264369 | A1 | 10/2009 | Szeto et al. |
| 2010/0190718 | A1 | 7/2010 | Schiller et al. |
| 2010/0204448 | A1 | 8/2010 | Szeto et al. |

FOREIGN PATENT DOCUMENTS

| | | |
|---|---|---|
| JP | 2006-505290 | 2/2006 |
| JP | 2006-516652 | 7/2006 |
| JP | 2007-518818 | 7/2007 |
| JP | 2009-509941 A | 3/2009 |
| WO | WO-96/40073 | 12/1996 |

(Continued)

OTHER PUBLICATIONS

Vincent, Yearbook of Intensive Care and Emergency Medicine, 2007.*
Kim et al, Reactive oxygen species, but not Ca2+ overloading, trigger pH and mitochondrial permeability transition-dependent death of adult rat myocytes after ischemia-reperfusion, Am J Physiol Heart Circ Physiol 290: H2024-H2034, 2006.*
Parihar et al, Oxidative stress and anti-oxidative mobilization in burn injury, burns 3 4 ( 2 0 0 8 ) 6-1 7.*
Park et al, Protection of burn-induced skin injuries by the flavonoid kaempferol, BMB reports 2010; 43(1): 46-51.*
Vercesi et al, The Role of Reactive Oxygen Species in Mitochondrial Permeability Transition, Bioscience Reports, vol. 17, No. 1, 1997.*
Alam, N.M. et al., "A Novel Peptide (MTP-131) that Improves Mitochondrial Function Reverses Visual Decline in Mouse Models of Metabolic Dysfunction Leading to Diabetes," American Diabetes Association, (2012), Poster Presentation (1 page).

(Continued)

*Primary Examiner* — James H Alstrum Acevedo
*Assistant Examiner* — Sergio Coffa
(74) *Attorney, Agent, or Firm* — Foley & Lardner LLP

(57) ABSTRACT

The disclosure relates to methods for treating a subject suffering from a burn injury or associated complications by administering to the subject an effective amount of an aromatic-cationic peptide. For example, a burn injury may be associated with distant pathophysiological effects, such as hypermetabolism, skeletal muscle dysfunction, and organ damage. The disclosure also relates to methods for protecting a subject from a burn injury by administering an effective amount of an aromatic-cationic peptide to a subject at risk of a burn injury.

9 Claims, 10 Drawing Sheets

(56) References Cited

FOREIGN PATENT DOCUMENTS

| WO | WO-99/15154 | 4/1999 |
|---|---|---|
| WO | WO-00/38651 | 7/2000 |
| WO | WO-2007/035640 | 3/2007 |

OTHER PUBLICATIONS

Alam, N.M. et al., "Reducing Mitochondrial Oxidative Stress to Treat Diabetes and Age-related Visual Decline," Society of Neuroscience, (2011), Poster Presentation (1 page).
Alam, Nazia et al., "A novel Peptide that Improves Mitochondrial Function Reverses Diabetes- and Age-Related Visual Decline," American Aging Association, (2012), Abstract (1 page).
Anderson, Ethan J. et al., "Mitochondrial H2O2 emission and cellular redox state link excess fat intake to insulin resistance in both rodents and humans," J. Clin. Invest., (Feb. 2009), vol. 119, No. 3, pp. 573-581.
Andersson, Daniel C. et al., "Mitochondrial production of reactive oxygen species contributes to the β-adrenergic stimulation of mouse cardiomycytes," J. Physiol., (2011), 589(7), pp. 1791-1801.
Apidianakis et al., "Involvement of Skeletal Muscle Gene Regulatory Network in Susceptibility to Wound Infection Following Trama," PLoS ONE Issue 12, e1356, pp. 1-9 (Dec. 2007).
Astrakas et al., "Proton NMR Spectroscopy Shows Lipids Accumulate in Skeletal Muscle in Response to Burn Trauma-induced Apoptosis," The FASEB Journal—Research Communication, vol. 19, pp. 1431-1140, (Sep. 2005).
Brown, David A. et al., "Bendavia, a mitochondria-targeting peptide, reduces reperfusion injury and reactive oxygen species levels through a mechanism independent of direct oxygen radical scavenging: A multicenter study," American Heart Association, (2012), Abstract (1 page).
Brown, David A., Ph.D., "Mitochondrial Derived Cardioprotection in Exercised Hearts: Role of Cardiac Glutathione," American College of Sports Medicine, (2012), DB Lab Presentation (28 pages).
Calkins, Marcus J. et al., "Impaired mitochondrial biogenesis, defective axonal transport of mitochondria, abnormal mitochondrial dynamics and synaptic degeneration in a mouse model of Alzheimer's disease," Hum. Mol. Genet., (2011), vol. 20, No. 23, pp. 4515-4529.
Cao, Mingfeng et al., "Mitochondria-targeted antioxidant attenuates high glucose-induced P38 MAPK pathway activation in human neuroblastoma cells," Mol. Med. Report., (2012), 5(4), pp. 929-934.
Carter, Edward A. et al., "Evaluation of the antioxidant peptide SS31 for treatment of burn-induced insulin resistance," Int. J. Mol. Med., (2011), 28(4), pp. 589-594.
Chen, Min et al., "Mitochondria-targeted Peptide MTP-131 Alleviates Mitochondrial Dysfunction and Oxidative Damage in Human Trabecular Meshwork Cells," Invest. Ophthalmol. & Vis. Sci., (Sep. 2011), vol. 52, No. 10, pp. 7027-7037.
Cho, Janghyun et al., "Potent mitochondria-targeted peptides reduce myocardial infarction in rats," Coron. Artery Dis., (2007), vol. 18, No. 3, pp. 215-220.
Cho, Sunghee et al., "A Novel Cell-permeable Antioxidant Peptide, SS31, Attenuates Ischemic Brain Injury by Down-regulating CD36," J. Biol. Chem., (Feb. 2007), vol. 282, No. 7, pp. 4634-4642.
Chonn, Arcadio et al., "Recent Advances in Liposomal Drug-Delivery Systems," Current Opinion in Biotechnology, (1995), vol. 6, pp. 698-708.
Dai, Dao-Fu et al., "Mitochondrial targeted antioxidant peptide ameliorates hypertensive cardiomyopathy," J. Am. Coll. Cardiol., (2011), vol. 58, No. 1, pp. 73-82.
Drin et al., "Studies on the internationalization mechanism of cationic cell-penetrating peptides," Journal of Biological Chemistry, vol. 278, No. 33, pp. 31192-31201 (2003).
Eirin, Alfonso et al., "A Mitochondrial Permeability Transition Pore Inhibitor Improves Renal Outcomes After Revascularization in Experimental Atherosclerotic Renal Artery Stenosis," J. Am. Heart Assoc., (2012), vol. 60, pp. 1242-1249; available at http://hyper.ahajournals.org/content/60/5/1242 and supplemental content available at http://hyper.ahajournals.org/content/suppl.2012/10/08/HYPERTENSIONAHA.112.199919.DC1.html (26 pages total).
Eirin, Alfonso et. al., "Chronic Treatment with Bendavia Preserves the Stenotic Kidney in Swine Atherosclerotic Renovascular Disease (ARVD)," American Society of Nephrology, (2012), Abstract & figures (2 pages).
Eirin, Alfonso et. al., "Mitochondrial Targeted Peptides Attenuate Myocardial Damage after Renal Revascularization in Experimental Atherosclerotic Renovascular Hypertension," American Society of Nephrology, (2012), Abstract & figures (2 pages).
Eirin, Alfonso, et. al., "MTP-131 reduces renal injury after percutaneous transluminal renal angioplasty (PTRA) in swine atherosclerotic renal artery stenosis (ARAS)," American Society of Nephrology, (2011), Poster Presentation (1 page).
Extended Search Report issued in European Application No. 10764805.7 mailed Nov. 8, 2012 (8 pages).
First Office Action received in Chinese Patent Application No. 201080021769.1 issued Jun. 13, 2013 (6 pages)—English translation only.
Gilliam, Laura A.A. et al., "Doxorubicin acts via mitochondrial ROS to stimulate catabolism in C2C12 myotubes," Am. J. Physiol. Cell Physiol., (Sep. 2011), 302(1), pp. C195-C202.
Gregoriadis, Gregory, "Engineering Liposomes for Drug Delivery: Progress and Problems," TIBTECH, (Dec. 1995), vol. 13, pp. 527-537.
Hale, Sharon L. et. al., "A Novel Mitochondrial Permeability Transition Pore Inhibitor, Bendavia, Reduces, Microvascular Obstruction (No-Reflow) due to Myocardial Ischemia/Reperfusion Injury in the Rabbit," Basic Cardiovascular Sciences, (2011), Poster Presentation (1 page).
Han, Zhaosheng et al., "Mitochondria-Derived Reactive Oxygen Species Mediate Heme Oxygenase-1 Expression in Sheared Endothelial Cells"; J. Pharmacol. Exp. Ther., (2009), vol. 329, No. 1, pp. 94-101.
Herve, et al., "On the Immunogenic Properties of Retro-Inverso Peptides: Total Retro-Inversion of T-Cell Epitopes Causes a Loss of Binding to MHC II Molecules," Molecular Immunology, 1997, vol. 34, No. 2, pp. 157-163.
Hosley et al., "Cardiovascular Effects of a u-selective Opioid Agonist (tyrosine-D-arginine-phenylalanine-lysine-NH2) in Fetal Sheep: Sites and Mechanisms of Action," Am J. Obstet. Gynecol, vol. 180, No. 5, pp. 1127-1130 (May 1999).
International Search Report and Written Opinion received in Application No. PCT/US2010/27953 dated Oct. 29, 2010 (10 pages).
Kaufmann PM, A Small Dose of Toxicology: Role of Mitochondrial Dysfunction in Hepatic and Skeletal Muscle Toxicity (Dissertation), Nov. 1, 2005, available at http://edc.unibas.ch/312/1/DissB_7162.pdf.
Kim, Jae-Sung et al., "Reactive oxygen species, but not Ca2+ overloading, trigger pH- and mitochondrial permeability transition-dependent death of adult rat myocytes after ischemia-reperfusion," Am J Physiol Heart Circ Physiol, (2006), 290, pp. H2024-H2034.
Kloner, Robert A. et al., "Reduction of Ischemia/Reperfusion Injury with Bendavia, a Mitochondria-Targeting Cytoprotective Peptide," J. Am. Heart Assoc., vol. 1, (2012), available at http://jaha.ahajournals.org/content/1/3/e001644 (14 pages).
Kloner, Robert A., et. al., "Bendavia, A Novel Mitochondrial-Targeted Cytoprotective Compound Reduces Ischemia/Reperfusion Injury: Experience in 3 Independent Laboratories," American Heart Association, (2011), Abstract (2 pages).
Lee, Hyung-yul et al., "Novel Mitochondria-Targeted Antioxidant Peptide Ameliorates Burn-Induced Apoptosis and Endoplasmic Reticulum Stress in the Skeletal Muscle of Mice," Shock, (2011), vol. 36, No. 6, pp. 580-585.
Li, Jianqiao et al., "Mitochondria-targeted antioxidant peptide SS31 attenuates high glucose-induced injury on human retinal endothelial cells," Biochem. & Biophys. Res. Commun., (2011), 404, pp. 349-356.
Liang, XL., et. al., "SS31 protects human RPE cells from oxidative damage and reduces laser-induced choroidal neovascularization," Association for Research in Vision and Opthamology, (2010), Poster Presentation (1 page).

(56) References Cited

OTHER PUBLICATIONS

Lichtenberg, Dov et al., "Liposomes: Preparation, Characterization and Preservation," Methods of Biochemical Analysis, (1988), vol. 33, pp. 337-462.
Liu, Shaoyi et. al., "Boosting mitochondrial function to minimize ischemia-reperfusion injury," Experimental Biology, (2011), Poster Presentation (1 page).
Liu, Shaoyi et. al., "Mitochondria-targeting peptide (SS-31) promotes rapid repair of actin cytoskeleton following ischemia and protects tubular epithelial cell architecture," American Society of Nephrology, (2012), Abstract (2), (1 page).
Ma, Qi et al., "Superoxide Flashes: Early Mitochondrial Signals for Oxidative Stress-Induced Apoptosis," J. Biol. Chem., (Aug. 2011), vol. 286, No. 31, pp. 27573-27581.
Malhi et al. Apoptosis and Necrosis in the Liver: A Tale of Two Deaths? Feb. 2006, Heptology 43(2): S31-S44.
Manczak, Maria et al., "Mitochondria-Targeted Antioxidants Protect Against Amyloid-β toxicity in Alzheimer's Disease Neurons," J. Alzheimer's Dis., (2010), 20, pp. S609-S631.
Marcinek, David J., et al., "Acute pharmacological intervention reverses mitochondrial deficits and improves function in aged skeletal muscle," American Aging Association, (2012), Abstract (1 page).
Min, Kisuk et al., "Mitochondrial-targeted antioxidants protect skeletal muscle against immobilization-induced muscle atrophy," J. Appl. Physiol., (2011), 111(5), pp. 1459-1466.
Min, Kisuk et. al., "Mitochondrial-targeted antioxidants attenuate immobilization-induced skeletal muscle atrophy," Experimental Biology, (2011), Abstract (1 page).
Mizuguchi, Hiroyuki et al., "Intratumor administration of fusogenic liposomes containing fragment A of diphtheria toxin suppresses tumor growth," Cancer Lett., (1996), vol. 100, Issue 1, pp. 63-69.
Mizuguchi, Yasunori et al., "A novel cell-permeable antioxidant peptide decreases renal tubular apoptosis and damage in unilateral ureteral obstruction," Am. J. Physiol. Renal Physiol., (2008), 295, pp. F1545-F1553.
Nieborowska-Skorska, Margaret et al., "Rac2-MRC-cIII-generated ROS cause genomic instability in chronic myeloid leukemia stem cells and primitive progenitors," Blood, (2012), vol. 119, No. 18, pp. 4253-4263.
Non-Final Office Action issued in U.S. Appl. No. 12/727,647 mailed Apr. 24, 2013 (12 pages).
Non-Final Office Action issued in U.S. Appl. No. 12/727,647 mailed Sep. 28, 2012 (17 pages).
Padfield et al., "Local and Distant Burn Injury Alter Immuno-Inflammatory Gene Expression in Skeletal Muscle," The Journal of Trauma Injury, Infection, and Critical Care vol. 61, No. 2, pp. 280-292 (Aug. 2006).
Padfield, Katie E. et al., "Burn Injury Causes Mitochondrial Dysfunction in Skeletal Muscle," PNAS, (Apr. 12, 2005), vol. 102, No. 15, pp. 5368-5373.
Parihar, Arti et al., "Oxidative stress and anti-oxidative mobilization in burn injury," Burns, (2008), vol. 34, pp. 6-17.
Park, Byoung Kwon et al., "Protection of burn-induced skin injuries by the flavonoid kaempferol," BMB Rep. (Jan. 2010), 43(1), pp. 46-51.
Petri, Susanne et al., "Cell-permeable peptide antioxidants as a novel therapeutic approach in a mouse model of amyotrophic lateral sclerosis", Journal of Neurochemistry, (2006), vol. 98, pp. 1141-1148.
Powers, Scott K. et al., "Mitochondria-targeted antioxidants protect against mechanical-ventilation-induced diaphragm weakness," Crit. Care Med., (2011), vol. 39, No. 7, pp. 1749-1759.
Putney, Scott D., "Encapsulation of proteins for improved delivery," Current Opinion in Chemical Biology, (1998), vol. 2, No. 4, pp. 548-552.
Rabinovitch, Peter, "Mitochondrial Oxidative Stress and Cardiac Aging," Basic Cardiovascular Sciences, (2011), Presentation (19 pages).
Reddy, K. Rajender, "Controlled-Release, Pegylation, Liposomal Formulations: New Mechanisms in the Delivery of Injectable Drugs," Ann Pharmacother., (Jul./Aug. 2000), vol. 34, pp. 915-923.
Reddy, P. Hemachandra, "Amyloid beta Toxicity, Mitochondrial Dysfunction and Synaptic Damage in Alzheimer's Disease: Implications for Mitochondria-Targeted Antioxidant Therapeutics," New York Academy of Sciences, (2010), Abstract (1 page).
Reddy, Tejaswini P. et al., "Toxicity of Neurons Treated with Herbicides and Neuroprotection by Mitochondria-Targeted Antioxidant SS31," Int. J. Environ. Res. & Public Health, (2011), 8, pp. 203-221.
Richard, et al., "Cell-penetrating Peptides," Journal of Biological Chemistry, (2003), 278(1), pp. 585-590.
Sabbah, Hani N. et al., "Acute Intravenous Infusion of Bendavia (MTP-131), A Novel Mitochondria-Targeting Peptide, Improves Left Ventricular Systolic Function in Dogs With Advanced Heart Failure," American Heart Association, (2012), Abstract (1 page).
Schiller et al., "Tipp: A highly potent and stable pseudopeptide opioid receptor antagonist with extraordinary selectivity," J. Med. Chem., 36:3182-3187, 1993.
Schiller et al., "Unsulfated C-terminal 7-peptide of cholecystokinin: a new ligand of the opiate receptor," Biochemical and Biophysical Research Communications, 85(4):1332-1338, 1978.
Schiller, et al., "Opioid peptide analogs with novel activity profiles as potential therapeutic agents for use in analgesia," Peptide Science—Present and Future, Proc. Int. Pept. Symp., 1st, Y. Shimonishi (ed), 1999, pp. 665-669.
Schiller, Peter W. et al., "Synthesis and In Vitro Opioid Activity Profiles of DALDA Analogues," European Journal of Medicinal Chemistry, (Oct. 2000), vol. 35, Issue 10, pp. 895-901.
Schwarze, et al., "In vivo protein transduction: intracellular delivery of biologically active proteins, compounds and DNA," Trends in Pharmacological Sciences, 21(2):45-48, 2000.
Sharma, Lokendra Kumar et al., "Mitochondrial respiratory complex I dysfunction promotes tumorigenesis through ROS alteration and AKT activation," Hum. Mol. Genet., (2011), vol. 20, No. 23, pp. 4605-4616.
Shimoyama, et al., "Antinociceptive and Respiratory Effects of Intrathecal H-Tyr-D-Arg-Phe-Lys-NH2 (DALDA) and [Dmt1] DALDA," The Journal of Pharmacology and Experimental Therapeutics, vol. 297, No. 1, Apr. 2001, pp. 364-371.
Shimoyama, et al., "Antinociceptive and Respiratory Effects of Intrathecal H-Tyr-D-Arg-Phe-Lys-NH2 (DALDA) and [Dmt1] DALDA," The Journal of Pharmacology and Experimental Therapeutics, vol. 297, No. 1, Apr. 2001, pp. 364-374.
Sloan, Ruben C. et al., "Mitochondrial permeability transition in the diabetic heart: Contributions of thiol redox state and mitochondrial calcium to augmented reperfusion injury," J. Mol. Cell. Cardiol., (2012), 52, pp. 1009-1018.
Song et al., "A Potent Opiate Agonist Protects Against Myocardial Stunning During Myocardial Ischemia and Reperfusion in Rats," Coronary Artery Disease, 16(6):407-410, 2005.
Szeto, "Development of Mitochondria-targeted Aromatic-cationic Peptides for Neurodegenerative Diseases," Ann. N.Y. Acad. Sci., (2008), 1147, pp. 112-121.
Szeto, et al., "Novel Therapies Targeting Inner Mitochondrial Membrane—from Discovery to Clinical Development", Pharm. Res., (2011), vol. 28, pp. 2669-2679.
Szeto, et al., "In Vivo Disposition of Dermorphin Analog (DALDA) in Nonpregnant and Pregnant Sheep," The Journal of Pharmacology and Experimental Therapeutics, vol. 284, No. 1, pp. 61-65 (1998).
Szeto, et al., "In Vivo Pharmacokinetics of Selective μ-Opioid Peptide Agonists," The Journal of Pharmacology and Experimental Therapeutics, vol. 298, No. 1, pp. 57-61 (2001).
Szeto, et al., "Respiratory Depression After Intravenous Administration of s-Selective Opioid Peptide Analogs," Peptides, vol. 20, 1999, pp. 101-105.
Szeto, Hazel H. "Mitochondria-targeted peptide antioxidants: Novel Neuroprotective Agents," The AAPS Journal, (2006), 8(3), Article 62, pp. E521-E531.
Szeto, Hazel H. et al., "Mitochondria-Targeted Peptide Accelerates ATP Recovery and Reduces Ischemic Kidney Injury," J. Am. Soc. Nephrol., (2011), 22, pp. 1041-1052.

(56) References Cited

OTHER PUBLICATIONS

Szeto, Hazel H. et. al., "Mitochondria-targeting peptide (SS-31, Bendavia®) prevents microvascular rarafaction, inflammation, and fibrosis caused by ischemia-reperfusion injury," American Society of Nephrology, (2012), Abstract (1 page).
Szeto, Hazel H., "Cell-permeable, Mitochondrial-targeted, Peptide Antioxidants," The AAPS Journal, (2006), 8(2) Article 32, pp. E277-E283.
Szeto, Hazel H., "Mitochondrial Protection as Strategy to treat Ischemia-Reperfusion Injury," American Society of Nephrology, (2010), Presentation (17 pages).
Szeto, Hazel H., "The development of a therapeutic peptide for mitochondrial protection—from bench to bedside," Experimental Biology, (2011), Poster Presentation (1 page).
Szeto, Hazel H., "Mitochondria-Targeted Cytoprotective Peptides for Ischemia-Reperfusion Injury," Antioxid. Redox Signal, (2008), vol. 10, No. 3, pp. 601-619.
Szeto, Hazel H., et. al., "Rapid Restoration of ATP by SS-31, an Inhibitor of Mitochondrial Permeability Transition, Prevents Tubular Cytoskeletal Rearrangement in Renal Ischemia-Reperfusion Injury," American Society of Nephrology, (2010), Poster Presentation (1 page).
Thomas, Dolca A. et al., "Mitochondrial Targeting with Antioxidant Peptide SS-31 Prevents Mitochondrial Depolarization, Reduces Islet Cell Apoptosis, Increases Islet Cell Yield, and Improves Posttransplantation Function," J. Am. Soc. Nephrol., (2007), 18, pp. 213-222.
Tiganis, Tony, "Reactive Oxygen Species & NAPDH Oxidases in Insulin Signalling," NOX Gordon Research Conference, (Jun. 3-8, 2012), Presentation (44 pages).
Tzika et al., "Microarray analysis suggests that burn injury results in mitochondrial dysfunction in human skeletal muscle," International Journal of Molecular Medicine vol. 24, pp. 387-392 (2009).
Tzika et al., "Reduced rate of adenosine triphosphate synthesis by in vivo 31P nuclear magnetic resonance spectroscopy and downregulation of PGC-1B in distal skeletal muscle following burn," International Journal of Molecular Medicine vol. 21, pp. 201-208 (2008).
Vercesi, Anibal E. et al., "The Role of Reactive Oxygen Species in Mitochondrial Permeability Transition," Bioscience Reports, (1997), vol. 17, No. 1, pp. 43-52.
Wang, Dantong et al., "Elevated Mitochondrial Reactive Oxygen Species Generation Affects the Immune Response via Hypoxia-Inducible Factor-1α in Long-Lived Mclk1+/− Mouse Mutants," J. Immunol., (2010), 184(2), pp. 582-590.
Weiner, Alan L., "Liposomes for Protein Delivery: Selecting Manufacture and Development Processes," Immunomethods, (1994), vol. 4., pp. 201-209.

Whiteman, Matthew et al., "Do Mitochondriotropic Antioxidants Prevent Chlorinative Stress-Induced Mitochondrial and Cellular Injury?" Antioxid. Redox Signal., (2008), vol. 10, No. 3, pp. 641-650.
Wu, et al., "A highly potent peptide analgesic that protects against ischemia-reperfusion-induced myocardial stunning," Am J Physiol Heart Circ Physiol., 283:H783-H791, 2002.
Yang, Lichuan et al., "Mitochondria Targeted Peptides Protect against 1-Methyl-4-Phenyl-1,2,3,6-Tetrahydropyridine Neurotoxicity," Antioxid Redox Signal., (2009), vol. 11, No. 9, pp. 2095-2104.
Zhang et al., "Burn-Related Metabolic and Signaling Changes in Rat Brain," Journal of Burn Care & Research vol. 29, No. 2, pp. 346-352 (Mar./Apr. 2008).
Zhao et al., "Cell-permeable peptide antioxidants targeted to inner mitochondrial membrane inhibit mitochondrial swelling, oxidative cell death, and reperfusion injury," J. Biol. Chem., 279(33):34682-34690, 2004.
Zhao, et al., "Transcellular transport of a highly polar 3+ net charge opioid tetrapeptide," J. Pharmacol. Exp. Ther., (2003), 304, pp. 425-432.
Zhao, Guo-Min et al., "Comparision of [Dmt1]DALDA and DAMGO in Binding and G Protein Activation at μ, δ, and κ Opioid Receptors," J Pharmacol Exp Ther., (2003), vol. 307, No. 3, pp. 947-954.
Zhao, Kesheng et al., "Mitochondria-targeted peptide prevents mitochondrial depolarization and apoptosis induced by tert-butyl hydroperoxide in neuronal cell lines," Biochem. Pharmacol., (2005), 70, pp. 1796-1806.
Zhu, Huaqing et al., "Histone Deacetylase-3 Activation Promotes Tumor Necrosis Factor-α (TNF-α) Expression in Cardiomyocytes during Lipopolysaccharide Stimulation," J. Biol. Chem., (Mar. 2010), vol. 285, No. 13, pp. 9429-9436.
Zhu, Huaqing et al., "MicroRNA-195 promotes palmitate-induced apoptosis in cardiomyocytes by down-regulating Sirt1," Cardiovasc. Res., (2011), 92, pp. 75-84.
Office Action received in Japanese Patent Application No. 2012-500991 issued Apr. 16, 2014 (3 pages).
First Office Action received in Chinese Patent Application No. 201310740133.8 issued Apr. 3, 2015, 8 pages—English translation only.
Hakvoort, T.E. et al., "Epidermal participation in post-burn hypertrophic scar development," Virchows Arch, (1999), 434, pp. 221-226.
Official Action received in European Patent Application No. 10764805.7 issued May 19, 2015, 4 pages.
Second Office Action received for Chinese Patent Application No. 201310740133.8 issued Feb. 1, 2016, 5 pages, English translation only.
Official Action received for Japanese Patent Application No. 2014-211820 issued Sep. 30, 2015, 8 pages.

* cited by examiner

Reduction of the nitroxide in control and immediately (0hr) post burn injury

METHODS FOR THE PREVENTION AND TREATMENT OF BURN INJURIES AND SECONDARY COMPLICATIONS

CROSS-REFERENCE TO RELATED APPLICATIONS

This application is a continuation of U.S. application Ser. No. 12/727,647, filed Mar. 19, 2010, which claims priority to U.S. Provisional Application No. 61/259,349, filed Nov. 9, 2009, U.S. Provisional Application No. 61/258,533, filed Nov. 5, 2009, U.S. Provisional Application No. 61/249,658, filed Oct. 8, 2009, and U.S. Provisional Application No. 61/162,060, filed Mar. 20, 2009, the entire contents of which are hereby incorporated by reference in their entirety.

GOVERNMENT SUPPORT

This invention was made with government support under 2P50 GM21700-27A awarded by the National Institute of Health. The government has certain rights in the invention.

TECHNICAL FIELD

The present technology relates generally to methods of preventing or treating burn injuries and associated complications by administration of an aromatic-cationic peptide.

BACKGROUND

The following description is provided to assist the understanding of the reader. None of the information provided or the references cited are admitted to be prior art to the present invention.

Burn trauma causes approximately two million injuries, 100,000 hospital admissions, and 10,000 deaths every year in the United States. In the past, many victims did not survive the initial resuscitation period. Current survival rates and clinical outcomes have progressively improved with the advent of aggressive burn wound excision techniques, graft therapy, and superior intensive care facilities, along with a better understanding of post-burn physiological factors and fluid requirements.

Systemic injury, such as the dysfunction or failure of an organ secondary to a severe burn injury and which is not attributable to the burn injury, remains a continuing source of morbidity and mortality. A severe burn is associated with release of inflammatory mediators which ultimately cause local and distant pathophysiological effects. Mediators including Reactive Oxygen Species (ROS) and Reactive Nitrogen Species (RNS) are increased in affected tissue, which are implicated in pathophysiological events observed in burn patients.

Free radicals have been found to have beneficial effects on antimicrobial action and wound healing. However, following a burn, there is an enormous production of ROS which is harmful and implicated in inflammation, systemic inflammatory response syndrome, immunosuppression, infection and sepsis, tissue damage and multiple organ failure. Thus, clinical response to burn is dependent on the balance between production of free radicals and its detoxification.

SUMMARY

In one aspect, the present disclosure provides methods for treating a subject suffering from a burn injury. The methods include administering to the subject an effective amount of an aromatic-cationic peptide. The aromatic-cationic peptide may have (a) at least one net positive charge; (b) a minimum of three amino acids; (c) a maximum of about twenty amino acids: (d) a relationship between the minimum number of net positive charges ($p_m$) and the total number of amino acid residues (r) wherein $3p_m$ is the largest number that is less than or equal to r+1; and (e) a relationship between the minimum number of aromatic groups (a) and the total number of net positive charges ($p_t$) wherein 3a is the largest number that is less than or equal to $p_t$+1, except that when a is 1, p, may also be 1. In one embodiment, the peptide is D-Arg-Dmt-Lys-Phe-NH$_2$ (SS-31).

In another aspect, the present disclosure provides a method of protecting a subject against the secondary effects of a burn injury. In one embodiment, peptide is administered to a subject following a burn injury to treat or ameliorate the incidence of hypermetabolism. In one embodiment, peptide is administered to a subject following burn injury to treat or ameliorate damage to the liver, which occurs secondary to the burn injury.

In another aspect, the present disclosure provides a method for protecting a subject against the primary effects of a burn by administering an effective amount of an aromatic-cationic peptide prior to exposure of the subject to an agent capable of causing a burn, e.g. sunlight (UV), thermal radiation, or radiation associated with radiotherapy. For example, the peptide may be administered topically to a subject at risk for receiving a burn.

In one embodiment, the systemic injury is organ dysfunction or failure, such as organ dysfunction or failure that affects one or more of the lung, liver, kidneys, or bowel. In one embodiment, the peptide is administered following a burn injury but prior to the onset of symptoms of organ dysfunction or failure. In another embodiment, the peptide is administered following the onset of symptoms of organ dysfunction or failure.

In one embodiment, the systemic injury is hypermetabolism. In one embodiment, the peptide is administered following a burn injury, but prior to the onset of symptoms of hypermetabolism. In another embodiment, the peptide is administered following the onset of symptoms hypermetabolism.

In one embodiment, the systemic injury is skeletal muscle dysfunction, such as skeletal muscle wasting and cachexia. In one embodiment, the peptide is administered following a burn injury, but prior to the onset of symptoms of skeletal muscle dysfunction. In another embodiment, the peptide is administered following the onset of symptoms skeletal muscle dysfunction.

In one aspect, the present disclosure provides methods for increasing ATP synthesis rate in a mammalian tissue, the method comprising administering to a subject an effective amount of an aromatic-cationic peptide. In one embodiment, the aromatic-cationic peptide is a peptide having the formula D-Arg-2'6'-dimethyltyrosine-Lys-Phe-NH$_2$.

In one embodiment, following administration of the peptide, the ATP synthesis rate in the mammalian tissue is increased compared to a control tissue. In one embodiment, the control tissue is tissue from a mammalian subject not administered the peptide. In one embodiment, increasing the ATP synthesis rate is by recovery of the mitochondrial redox status. In one embodiment, increasing the ATP synthesis rate is by increasing the expression or activity of the peroxisome proliferator activated receptor-gamma coactivator-1β (PGC-1β) protein.

In one aspect, the present disclosure provides methods for treating a disease or condition characterized by a reduced ATP synthesis rate, the method comprising administering to a mammal in need thereof an effective amount of an aromatic-cationic peptide. In one embodiment, the aromatic-cationic peptide is a peptide having the formula D-Arg-2'6'-dimethyltyrosine-Lys-Phe-NH$_2$. In one embodiment, the disease or condition is a burn injury.

In one embodiment, the peptide is defined by formula I:

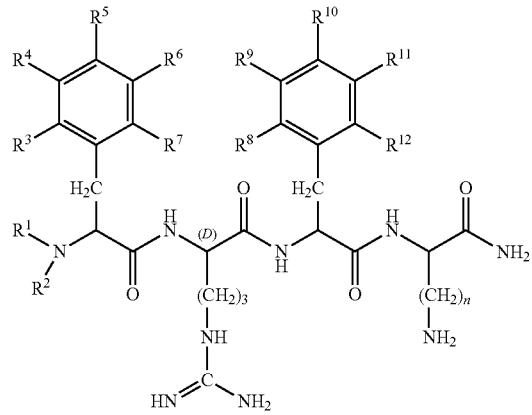

wherein $R^1$ and $R^2$ are each independently selected from
  (i) hydrogen;
  (ii) linear or branched $C_1$-$C_6$ alkyl;

(iii)

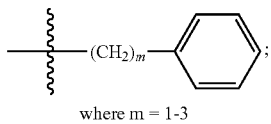

where m = 1-3

(iv)

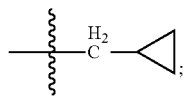

(v)

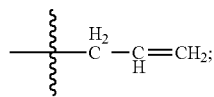

$R^3$, $R^4$, $R^5$, $R^6$, $R^7$, $R^8$, $R^9$, $R^{10}$, $R^{11}$ and $R^{12}$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo; and n is an integer from 1 to 5.

In a particular embodiment, $R^1$, $R^2$, $R^3$, $R^4$, $R^5$, $R^6$, $R^7$, $R^8$, $R^9$, $R^{10}$, $R^{11}$, and $R^{12}$ are all hydrogen; and n is 4. In another embodiment, $R^1$, $R^2$, $R^3$, $R^4$, $R^5$, $R^6$, $R^7$, $R^8$, $R^9$, and $R^{11}$ are all hydrogen; $R^8$ and $R^{12}$ are methyl; $R^{10}$ is hydroxyl; and n is 4.

In one embodiment, the peptide is defined by formula II:

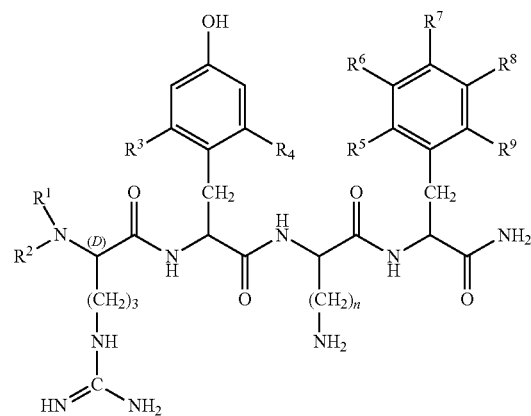

wherein $R^1$ and $R^2$ are each independently selected from
  (i) hydrogen;
  (ii) linear or branched $C_1$-$C_6$ alkyl;

(iii)

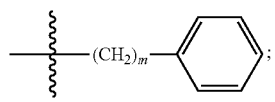

where m = 1-3

(iv)

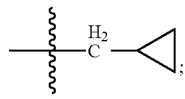

(v)

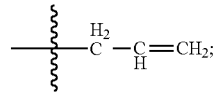

$R^3$ and $R^4$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo;
$R^5$, $R^6$, $R^7$, $R^8$, and $R^9$ are each independently selected from
  (i) hydrogen;
  (ii) linear or branched $C_1$-$C_6$ alkyl;
  (iii) $C_1$-$C_6$ alkoxy;
  (iv) amino;
  (v) $C_1$-$C_4$ alkylamino;
  (vi) $C_1$-$C_4$ dialkylamino;
  (vii) nitro;
  (viii) hydroxyl;
  (ix) halogen, where "halogen" encompasses chloro, fluoro, bromo, and iodo; and n is an integer from 1 to 5.

In a particular embodiment, $R^1$ and $R^2$ are hydrogen; $R^3$ and $R^4$ are methyl; $R^5$, $R^6$, $R^7$, $R^8$, and $R^9$ are all hydrogen; and n is 4.

DETAILED DESCRIPTION

Figure 1:
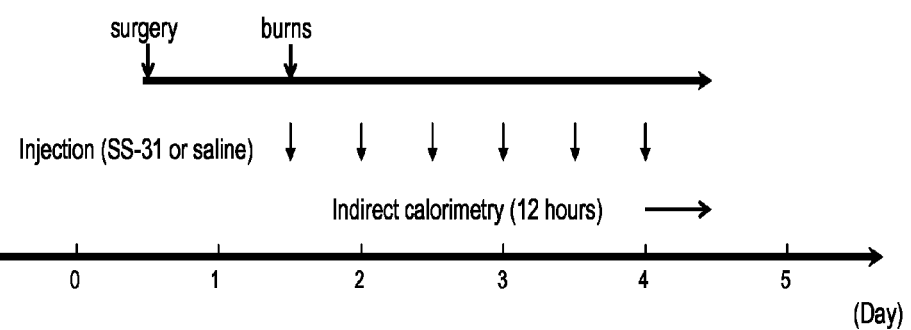
FIG. 1 is a flow chart showing the protocol and dosing schedule for the study presented in Example 1.

The present disclosure is based on the surprising discovery by the inventors that certain aromatic-cationic peptides can treat or ameliorate the local and distant pathophysiological effects of burn injury, including, but not limited to, hypermetabolism and organ damage. It is to be appreciated that certain aspects, modes, embodiments, variations, and features of the invention are described below in various levels of detail in order to provide a substantial understanding of the present invention.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y., 1989); *DNA Cloning: A Practical Approach*, Vols. I and II, Glover, Ed. (1985); *Oligonucleotide Synthesis*, Gait, Ed. (1984); *Nucleic Acid Hybridization*. Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, NY, 1987); and *Meth. Enzmmol.*, Vols. 154 and 155, Wu & Grossman, and Wu, Eds., respectively.

The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a," "an," and "the" include plural referents unless the content clearly dictates otherwise. For example, reference to "a cell" includes a combination of two or more cells, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the enumerated value.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the terms "burn" or "burn conditions" are intended to encompass the full range of such conditions, including those resulting from: excessive exposure to radiation, e.g. solar radiation resulting in sunburn, thermal radiation, welding flash, fires, electrical discharge, contact with chemicals, friction, contact with very hot objects such as cooking apparatus elements or hot fluids such as scalding water, hot oil, etc.

As used herein, the term "effective amount" refers to a quantity sufficient to achieve a desired therapeutic and/or prophylactic effect, e.g., an amount which results in the prevention of, or a decrease in, a burn injury or one or more conditions associated with a burn injury. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of the injury. The skilled artisan will be able to determine appropriate dosages depending on these and other factors. The compositions can also be administered in combination with one or more additional therapeutic compounds.

An "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with therapeutic uses of the agent. Such interfering materials may include enzymes, hormones and other proteinaceous and nonproteinaceous solutes.

As used herein, the term "medical condition" includes, but is not limited to, any condition or disease manifested as one or more physical and/or psychological symptoms for which treatment and/or prevention is desirable, and includes previously and newly identified diseases and other disorders. For example, a medical condition may be a burn injury or any associated conditions or complications.

The term "organ" as used herein refers to a part or structure of the body which is adapted for a special function or functions, and includes, but is not limited to, the lungs, the liver, the kidneys, and the bowel, including the stomach and intestines. In particular, it is contemplated that organs which are particularly susceptible to dysfunction and failure arising from a burn to another part of the body are encompassed by this term.

The term "organ dysfunction" as used herein refers to a continuum of indications ranging from a minor perturbation in the normal function(s) of an organ to "organ failure," i.e., the cessation of sufficient organ output to sustain life. Various diagnostic and clinical markers known in the art can be used to assess the function of organs.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts, as well as in a voluminous research literature.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, the words "protect" or "protecting" refer to decreasing the likelihood and/or risk that the subject treated with a peptide of the invention will develop a given disease or disorder, e.g., a burn injury or associated conditions or complications. Typically, the likelihood of developing the disease or disorder is considered to be reduced if the likelihood is decreased by at least about 10%, preferably at least about 25%, more preferably at least about 50%, even more preferably at least about 75%, and most preferably at least about 90%, in comparison to the likelihood and/or risk that the same subject untreated with a peptide of the invention will develop an injury. In particular embodiments, the peptides protect a subject against distant pathophysiological effects of burn injury when the peptides are administered after a subject receives a burn injury, but before the onset of symptoms of systemic injury. In one embodiment, the peptides will protect a subject from the primary burn injury when administered topically or systemically prior to the subject's exposure to an agent capable of causing a burn, e.g., sunlight or radiation.

The term "subject" as used herein refers to a member of any vertebrate species. The methods of the presently disclosed subject matter are particularly useful for warm-blooded vertebrates. Provided herein is the treatment of mammals such as humans, as well as those mammals of importance due to being endangered, of economic importance (animals raised on farms for consumption by humans) and/or social importance (animals kept as pets or in zoos) to humans. In particular embodiments, the subject is a human.

As used herein, the terms "treating," "treatment," or "alleviation" refer to both therapeutic treatment and prophylactic or preventative measures, wherein the object is to prevent or slow down (lessen) the targeted pathologic condition or disorder. A subject is successfully "treated" for a disease or condition if, after receiving a therapeutic amount of the aromatic-cationic peptides according to the methods described herein, the subject shows observable and/or measurable reduction in or absence of one or more signs and symptoms of a particular disease or condition. For example, for a burn injury, treatment or prevention may include a reduction in the size or severity of the burn wound; a reduction in hypermetabolism, liver damage or function; and improved effects on other organ systems. It is also to be appreciated that the various modes of treatment or prevention of medical conditions as described are intended to mean "substantial", which includes total but also less than total treatment or prevention, and wherein some biologically or medically relevant result is achieved.

Peptides

The aromatic-cationic peptides useful in the present methods are water-soluble and highly polar. Despite these properties, the peptides can readily penetrate cell membranes.

The aromatic-cationic peptides useful in the present methods include a minimum of three amino acids, and preferably include a minimum of four amino acids, covalently joined by peptide bonds. The maximum number of amino acids present in the aromatic-cationic peptides of the present methods is about twenty amino acids covalently joined by peptide bonds. Preferably, the maximum number of amino acids is about twelve, more preferably about nine, and most preferably about six. Optimally, the number of amino acids present in the peptides is four.

The amino acids of the aromatic-cationic peptides can be any amino acid. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea.

The peptides can optionally contain one or more non-naturally occurring amino acids. The non-naturally occurring amino acids may be L-, dextrorotatory (D), or mixtures thereof. The peptide may have no amino acids that are naturally occurring. Non-naturally occurring amino acids are those amino acids that typically are not synthesized in normal metabolic processes in living organisms, and do not naturally occur in proteins. In addition, the non-naturally occurring amino acids are not recognized by common proteases.

The non-naturally occurring amino acid can be present at any position in the peptide. For example, the non-naturally occurring amino acid can be at the N-terminus, the C-terminus, or at any position between the N-terminus and the C-terminus. The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenylacetic acid, and γ-phenyl-β-aminobutyric acid. Non-naturally occurring amino acids also include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e. alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva), norleucine (Nle), and hydroxyproline (Hyp).

Another example of a modification of an amino acid is the derivatization of a carboxyl group of an aspartic acid or a glutamic acid residue of the peptide. One example of derivatization is amidation with ammonia or with a primary or secondary amine, e.g., methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant, and more preferably insensitive, to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, less than four, less than three, less than two contiguous L-amino acids recognized by common proteases, irrespective of whether the amino acids are naturally or non-naturally occurring. If the peptide contains protease sensitive sequences of amino acids, at least one of the amino acids may be a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

In suitable embodiments, the aromatic-cationic peptides have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid. Typically, a peptide has a positively charged N-terminal amino group and a negatively charged C-terminal carboxyl group. The charges cancel each other out at physiological pH.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

| Amino acid number and net positive charges ($3p_m \leq p + 1$) | | | | | | | | | | | | | | | | | | | |
|---|---|---|---|---|---|---|---|---|---|---|---|---|---|---|---|---|---|---|---|
| (r) | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

| Amino acid number and net positive charges ($2p_m \leq p + 1$) | | | | | | | | | | | | | | | | | | | |
|---|---|---|---|---|---|---|---|---|---|---|---|---|---|---|---|---|---|---|---|
| (r) | 3 | 4 | 5 | 6 | 7 | 8 | 9 | 10 | 11 | 12 | 13 | 14 | 15 | 16 | 17 | 18 | 19 | 20 |
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, preferably, a minimum of two net positive charges and more preferably a minimum of three net positive charges. In suitable embodiments, the aromatic-cationic peptides have a minimum number of aromatic groups in comparison to the total number of net positive charges ($p_t$). The minimum number of aromatic groups will be referred to below as (a).

Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

In one embodiment, the aromatic-cationic peptides have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

| Aromatic groups and net positive charges ($3a \leq p_t + 1$ or $a = p_t = 1$) | | | | | | | | | | | | | | | | | | | |
|---|---|---|---|---|---|---|---|---|---|---|---|---|---|---|---|---|---|---|---|
| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

TABLE 4

| Aromatic groups and net positive charges ($2a \leq p_t + 1$ or $a = p_t = 1$) | | | | | | | | | | | | | | | | | | | |
|---|---|---|---|---|---|---|---|---|---|---|---|---|---|---|---|---|---|---|---|
| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, may be amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group.

The free carboxylate groups of the asparagine, glutamine, aspartic acid, and glutamic acid residues not occurring at the C-terminus of the aromatic-cationic peptides of the present invention may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following exemplary peptides:

```
Lys-D-Arg-Tyr-NH₂

Phe-D-Arg-His

D-Tyr-Trp-Lys-NH₂

Trp-D-Lys-Tyr-Arg-NH₂

Tyr-His-D-Gly-Met

Phe-Arg-D-His-Asp

Tyr-D-Arg-Phe-Lys-Glu-NH₂

Met-Tyr-D-Lys-Phe-Arg

D-His-Glu-Lys-Tyr-D-Phe-Arg

Lys-D-Gln-Tyr-Arg-D-Phe-Trp-NH₂

Phe-D-Arg-Lys-Trp-Tyr-D-Arg-His

Gly-D-Phe-Lys-Tyr-His-D-Arg-Tyr-NH₂

Val-D-Lys-His-Tyr-D-Phe-Ser-Tyr-Arg-NH₂

Trp-Lys-Phe-D-Asp-Arg-Tyr-D-His-Lys

Lys-Trp-D-Tyr-Arg-Asn-Phe-Tyr-D-His-NH₂

Thr-Gly-Tyr-Arg-D-His-Phe-Trp-D-His-Lys

Asp-D-Trp-Lys-Tyr-D-His-Phe-Arg-D-Gly-Lys-NH₂

D-His-Lys-Tyr-D-Phe-Glu-D-Asp-D-His-D-Lys-Arg-Trp-NH₂

Ala-D-Phe-D-Arg-Tyr-Lys-D-Trp-His-D-Tyr-Gly-Phe

Tyr-D-Lhs-Phe-D-Arg-Asp-Lys-D-Arg-His-Trp-D-His-Phe

Phe-Phe-D-Tyr-Arg-Glu-Asp-D-Lys-Arg-D-Arg-His-Phe-NH₂

Phe-Try-Lys-D-Arg-Trp-His-D-Lys-D-Lys-Glu-Arg-D-Tyr-Thr

Tyr-Asp-D-Lys-Tyr-Phe-D-Lys-D-Arg-Phe-Pro-D-Tyr-His-Lys

Glu-Arg-D-Lys-Tyr-D-Val-Phe-D-His-Trp-Arg-D-Gly-Tyr-Arg-D-Met-NH₂

Arg-D-Leu-D-Tyr-Phe-Lys-Glu-D-Lys-Arg-D-Trp-Lys-D-Phe-Tyr-D-Arg-Gly

D-Glu-Asp-Lys-D-Arg-D-His-Phe-Phe-D-Val-Tyr-Arg-Tyr-D-Tyr-Arg-His-Phe-NH₂

Asp-Arg-D-Phe-Cys-Phe-D-Arg-D-Lys-Tyr-Arg-D-Tyr-Trp-D-His-Tyr-D-Phe-Lys-Phe

His-Tyr-D-Arg-Trp-Lys-Phe-D-Asp-Ala-Arg-Cys-D-Tyr-His-Phe-D-Lys-Tyr-His-Ser-NH₂

Gly-Ala-Lys-Phe-D-Lys-Glu-Arg-Tyr-His-D-Arg-D-Arg-Asp-Tyr-Trp-D-His-Trp-His-D-Lys-Asp

Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH₂
```

In some embodiments, peptides are those peptides which have a tyrosine residue or a tyrosine derivative. Suitable derivatives of tyrosine include 2'-methyltyrosine (Mmt); 2',6'-dimethyltyrosine (2'6'Dmt); 3',5'-dimethyltyrosine (3'5'Dmt); N,2',6'-trimethyltyrosine (Tmt); and 2'-hydroxy-6'-methyltryosine (Hmt).

In one embodiment, the peptide has the formula Tyr-D-Arg-Phe-Lys-NH$_2$ (referred to herein as SS-01). SS-01 has a net positive charge of three, contributed by the amino acids tyrosine, arginine, and lysine and has two aromatic groups contributed by the amino acids phenylalanine and tyrosine. The tyrosine of SS-01 can be a modified derivative of tyrosine such as in 2',6'-dimethyltyrosine to produce the compound having the formula 2',6'-Dmt-D-Arg-Phe-Lys-NH$_2$ (referred to herein as SS-02).

In a suitable embodiment, the amino acid residue at the N-terminus is arginine. An example of such a peptide is D-Arg-2'6'Dmt-Lys-Phe-NH (referred to herein as SS-31). In another embodiment, the amino acid at the N-terminus is phenylalanine or its derivative.

Derivatives of phenylalanine include 2'-methylphenylalanine (Mmp), 2',6'-dimethylphenylalanine (Dmp), N,2',6'-trimethylphenylalanine (Tmp), and 2'-hydroxy-6'-methylphenylalanine (Hmp). An example of such a peptide is Phe-D-Arg-Phe-Lys-NH$_2$ (referred to herein as SS-20). In one embodiment, the amino acid sequence of SS-02 is rearranged such that Dmt is not at the N-terminus. An example of such an aromatic-cationic peptide has the formula D-Arg-2'6'Dmt-Lys-Phe-NH$_2$ (SS-31).

In yet another embodiment, the aromatic-cationic peptide has the formula Phe-D-Arg-Dmt-Lys-NH$_2$ (referred to herein as SS-30). Alternatively, the N-terminal phenylalanine can be a derivative of phenylalanine such as 2',6'-dimethylphenylalanine (2'6'Dmp). SS-01 containing 2',6'-dimethylphenylalanine at amino acid position one has the formula 2',6'-Dmp-D-Arg-Dmt-Lys-NH$_2$.

Suitable substitution variants of the peptides include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group are generally more likely to alter the characteristics of the original peptide. Examples of peptides include, but are not limited to, the aromatic-cationic peptides shown in Table 5.

TABLE 5

Examples of Aromatic-Cationic Peptides

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | NH$_2$ |
| D-Arg | Dmt | Phe | Lys | NH$_2$ |
| D-Arg | Phe | Lys | Dmt | NH$_2$ |
| D-Arg | Phe | Dmt | Lys | NH$_2$ |
| D-Arg | Lys | Dmt | Phe | NH$_2$ |
| D-Arg | Lys | Phe | Dmt | NH$_2$ |
| D-Arg | Dmt | Lys | Phe | NH$_2$ |
| D-Arg | Dmt | Lys | Phe | NH$_2$ |
| D-Arg | Dmt | Lys | Phe | NH$_2$ |
| D-Arg | Dmt | Lys | Phe | NH$_2$ |
| D-Arg | Dmt | Lys | Phe | NH$_2$ |
| Phe | Lys | Dmt | D-Arg | NH$_2$ |
| Phe | Lys | D-Arg | Dmt | NH$_2$ |
| Phe | D-Arg | Phe | Lys | NH$_2$ |
| Phe | D-Arg | Phe | Lys | NH$_2$ |
| Phe | D-Arg | Phe | Lys | NH$_2$ |
| Phe | D-Arg | Phe | Lys | NH$_2$ |
| Phe | D-Arg | Phe | Lys | NH$_2$ |
| Phe | D-Arg | Dmt | Lys | NH$_2$ |
| Phe | D-Arg | Dmt | Lys | NH$_2$ |
| Phe | D-Arg | Dmt | Lys | NH$_2$ |
| Phe | D-Arg | Dmt | Lys | NH$_2$ |
| Phe | D-Arg | Dmt | Lys | NH$_2$ |
| Phe | D-Arg | Dmt | Lys | NH$_2$ |
| Phe | D-Arg | Lys | Dmt | NH$_2$ |
| Phe | Dmt | D-Arg | Lys | NH$_2$ |
| Phe | Dmt | Lys | D-Arg | NH$_2$ |
| Lys | Phe | D-Arg | Dmt | NH$_2$ |
| Lys | Phe | Dmt | D-Arg | NH$_2$ |
| Lys | Dmt | D-Arg | Phe | NH$_2$ |
| Lys | Dmt | Phe | D-Arg | NH$_2$ |
| Lys | D-Arg | Phe | Dmt | NH$_2$ |
| Lys | D-Arg | Dmt | Phe | NH$_2$ |
| D-Arg | Dmt | D-Arg | Phe | NH$_2$ |
| D-Arg | Dmt | D-Arg | Dmt | NH$_2$ |
| D-Arg | Dmt | D-Arg | Tyr | NH$_2$ |
| D-Arg | Dmt | D-Arg | Trp | NH$_2$ |
| Trp | D-Arg | Phe | Lys | NH$_2$ |
| Trp | D-Arg | Tyr | Lys | NH$_2$ |
| Trp | D-Arg | Trp | Lys | NH$_2$ |
| Trp | D-Arg | Dmt | Lys | NH$_2$ |
| D-Arg | Trp | Lys | Phe | NH$_2$ |
| D-Arg | Trp | Phe | Lys | NH$_2$ |
| D-Arg | Trp | Lys | Dmt | NH$_2$ |
| D-Arg | Trp | Dmt | Lys | NH$_2$ |
| D-Arg | Lys | Trp | Phe | NH$_2$ |
| D-Arg | Lys | Trp | Dmt | NH$_2$ |
| Cha | D-Arg | Phe | Lys | NH$_2$ |
| Ala | D-Arg | Phe | Lys | NH$_2$ |

Cha = cyclohexylalanine

Under certain circumstances, it may be advantageous to use a peptide that also has opioid receptor agonist activity. Examples of mu-opioid analogs include, but are not limited to, the aromatic-cationic peptides shown in Table 6.

TABLE 6

Aromatic-Cationic Peptides with Opioid Receptor Agonist Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | NH$_2$ |
| Tyr | D-Arg | Phe | Orn | NH$_2$ |
| Tyr | D-Arg | Phe | Dab | NH$_2$ |
| Tyr | D-Arg | Phe | Dap | NH$_2$ |
| Tyr | D-Arg | Phe | Lys | NH$_2$ |
| 2'6'Dmt | D-Arg | Phe | Lys | NH$_2$ |
| 2'6'Dmt | D-Arg | Phe | Lys | NH$_2$ |
| 2'6'Dmt | D-Arg | Phe | Lys-NH(CH$_2$)$_2$-NH-dns | NH$_2$ |
| 2'6'Dmt | D-Arg | Phe | Lys-NH(CH$_2$)$_2$-NH-atn | NH$_2$ |
| 2'6'Dmt | D-Arg | Phe | dnsLys | NH$_2$ |
| 2'6'Dmt | D-Cit | Phe | Lys | NH$_2$ |
| 2'6'Dmt | D-Cit | Phe | Lys | NH$_2$ |

TABLE 6-continued

Aromatic-Cationic Peptides with Opioid Receptor Agonist Activity

| Amino Acid Position 1 | Amino Acid Position 2 | Amino Acid Position 3 | Amino Acid Position 4 | C-Terminal Modification |
|---|---|---|---|---|
| 2'6'Dmt | D-Cit | Phe | Ahp | NH$_2$ |
| 2'6'Dmt | D-Arg | Phe | Orn | NH$_2$ |
| 2'6'Dmt | D-Arg | Phe | Dab | NH$_2$ |
| 2'6'Dmt | D-Arg | Phe | Dap | NH$_2$ |
| 2'6'Dmt | D-Arg | Phe | Ahp(2-aminoheptanoic acid) | NH$_2$ |
| Bio-2'6'Dmt | D-Arg | Phe | Lys | NH$_2$ |
| 3'5'Dmt | D-Arg | Phe | Lys | NH$_2$ |
| 3'5'Dmt | D-Arg | Phe | Orn | NH$_2$ |
| 3'5'Dmt | D-Arg | Phe | Dab | NH$_2$ |
| 3'5'Dmt | D-Arg | Phe | Dap | NH$_2$ |
| Tyr | D-Arg | Tyr | Lys | NH$_2$ |
| Tyr | D-Arg | Tyr | Orn | NH$_2$ |
| Tyr | D-Arg | Tyr | Dab | NH$_2$ |
| Tyr | D-Arg | Tyr | Dap | NH$_2$ |
| 2'6'Dmt | D-Arg | Tyr | Lys | NH$_2$ |
| 2'6'Dmt | D-Arg | Tyr | Orn | NH$_2$ |
| 2'6'Dmt | D-Arg | Tyr | Dab | NH$_2$ |
| 2'6'Dmt | D-Arg | Tyr | Dap | NH$_2$ |
| 2'6'Dmt | D-Arg | 2'6'Dmt | Lys | NH$_2$ |
| 2'6'Dmt | D-Arg | 2'6'Dmt | Orn | NH$_2$ |
| 2'6'Dmt | D-Arg | 2'6'Dmt | Dab | NH$_2$ |
| 2'6'Dmt | D-Arg | 2'6'Dmt | Dap | NH$_2$ |
| 3'5'Dmt | D-Arg | 3'5'Dmt | Arg | NH$_2$ |
| 3'5'Dmt | D-Arg | 3'5'Dmt | Lys | NH$_2$ |
| 3'5'Dmt | D-Arg | 3'5'Dmt | Orn | NH$_2$ |
| 3'5'Dmt | D-Arg | 3'5'Dmt | Dab | NH$_2$ |
| 2'6'Dmt | D-Arg | 2'6'Dmt | Lys | NH$_2$ |
| Tyr | D-Lys | Phe | Dap | NH$_2$ |
| Tyr | D-Lys | Phe | Arg | NH$_2$ |
| Tyr | D-Lys | Phe | Arg | NH$_2$ |
| Tyr | D-Lys | Phe | Lys | NH$_2$ |
| Tyr | D-Lys | Phe | Orn | NH$_2$ |
| 2'6'Dmt | D-Lys | Phe | Dab | NH$_2$ |
| 2'6'Dmt | D-Lys | Phe | Dap | NH$_2$ |
| 2'6'Dmt | D-Lys | Phe | Arg | NH$_2$ |
| 2'6'Dmt | D-Lys | Phe | Lys | NH$_2$ |
| 3'5'Dmt | D Lys | Phe | Orn | NH$_2$ |
| 3'5'Dmt | D-Lys | Phe | Dab | NH$_2$ |
| 3'5'Dmt | D-Lys | Phe | Dap | NH$_2$ |
| 3'5'Dmt | D-Lys | Phe | Arg | NH$_2$ |
| 3'5'Dmt | D-Lys | Phe | Arg | NH$_2$ |
| Tyr | D-Lys | Tyr | Lys | NH$_2$ |
| Tyr | D-Lys | Tyr | Orn | NH$_2$ |
| Tyr | D-Lys | Tyr | Dab | NH$_2$ |
| Tyr | D-Lys | Tyr | Dap | NH$_2$ |
| 2'6'Dmt | D-Lys | Tyr | Lys | NH$_2$ |
| 2'6'Dmt | D-Lys | Tyr | Orn | NH$_2$ |
| 2'6'Dmt | D-Lys | Tyr | Dab | NH$_2$ |
| 2'6'Dmt | D-Lys | Tyr | Dap | NH$_2$ |
| 2'6'Dmt | D-Lys | 2'6'Dmt | Lys | NH$_2$ |
| 2'6'Dmt | D-Lys | 2'6'Dmt | Orn | NH$_2$ |
| 2'6'Dmt | D-Lys | 2'6'Dmt | Dab | NH$_2$ |
| 2'6'Dmt | D-Lys | 2'6'Dmt | Dap | NH$_2$ |
| 2'6'Dmt | D-Arg | Phe | dnsDap | NH$_2$ |
| 2'6'Dmt | D-Arg | Phe | atnDap | NH$_2$ |
| 3'5'Dmt | D-Lys | 3'5'Dmt | Lys | NH$_2$ |
| 3'5'Dmt | D-Lys | 3'5'Dmt | Orn | NH$_2$ |
| 3'5'Dmt | D-Lys | 3'5'Dmt | Dab | NH$_2$ |
| 3'5'Dmt | D-Lys | 3'5'Dmt | Dap | NH$_2$ |
| Tyr | D-Lys | Phe | Arg | NH$_2$ |
| Tyr | D-Orn | Phe | Arg | NH$_2$ |
| Tyr | D-Dab | Phe | Arg | NH$_2$ |
| Tyr | D-Dap | Phe | Arg | NH$_2$ |
| 2'6'Dmt | D-Arg | Phe | Arg | NH$_2$ |
| 2'6'Dmt | D-Lys | Phe | Arg | NH$_2$ |
| 2'6'Dmt | D-Orn | Phe | Arg | NH$_2$ |
| 2'6'Dmt | D-Dab | Phe | Arg | NH$_2$ |
| 3'5'Dmt | D-Dap | Phe | Arg | NH$_2$ |
| 3'5'Dmt | D-Arg | Phe | Arg | NH$_2$ |
| 3'5'Dmt | D-Lys | Phe | Arg | NH$_2$ |
| 3'5'Dmt | D-Orn | Phe | Arg | NH$_2$ |
| Tyr | D-Lys | Tyr | Arg | NH$_2$ |
| Tyr | D-Orn | Tyr | Arg | NH$_2$ |
| Tyr | D-Dab | Tyr | Arg | NH$_2$ |
| Tyr | D-Dap | Tyr | Arg | NH$_2$ |
| 2'6'Dmt | D-Arg | 2'6'Dmt | Arg | NH$_2$ |
| 2'6'Dmt | D-Lys | 2'6'Dmt | Arg | NH$_2$ |
| 2'6'Dmt | D-Orn | 2'6'Dmt | Arg | NH$_2$ |
| 2'6'Dmt | D-Dab | 2'6'Dmt | Arg | NH$_2$ |
| 3'5'Dmt | D-Dap | 3'5'Dmt | Arg | NH$_2$ |
| 3'5'Dmt | D-Arg | 3'5'Dmt | Arg | NH$_2$ |
| 3'5'Dmt | D-Lys | 3'5'Dmt | Arg | NH$_2$ |
| 3'5'Dmt | D-Orn | 3'5'Dmt | Arg | NH$_2$ |
| Mmt | D-Arg | Phe | Lys | NH$_2$ |
| Mmt | D-Arg | Phe | Orn | NH$_2$ |
| Mmt | D-Arg | Phe | Dab | NH$_2$ |
| Mmt | D-Arg | Phe | Dap | NH$_2$ |
| Tmt | D-Arg | Phe | Lys | NH$_2$ |
| Tmt | D-Arg | Phe | Orn | NH$_2$ |
| Tmt | D-Arg | Phe | Dab | NH$_2$ |
| Tmt | D-Arg | Phe | Dap | NH$_2$ |
| Hmt | D-Arg | Phe | Lys | NH$_2$ |
| Hmt | D-Arg | Phe | Orn | NH$_2$ |
| Hmt | D-Arg | Phe | Dab | NH$_2$ |
| Hmt | D-Arg | Phe | Dap | NH$_2$ |
| Mmt | D-Lys | Phe | Lys | NH$_2$ |
| Mmt | D-Lys | Phe | Orn | NH$_2$ |
| Mmt | D-Lys | Phe | Dab | NH$_2$ |
| Mmt | D-Lys | Phe | Dap | NH$_2$ |
| Mmt | D-Lys | Phe | Arg | NH$_2$ |
| Tmt | D-Lys | Phe | Lys | NH$_2$ |
| Tmt | D-Lys | Phe | Orn | NH$_2$ |
| Tmt | D-Lys | Phe | Dab | NH$_2$ |
| Tmt | D-Lys | Phe | Dap | NH$_2$ |
| Tmt | D-Lys | Phe | Arg | NH$_2$ |
| Hmt | D-Lys | Phe | Lys | NH$_2$ |
| Hmt | D-Lys | Phe | Orn | NH$_2$ |
| Hmt | D-Lys | Phe | Dab | NH$_2$ |
| Hmt | D-Lys | Phe | Dap | NH$_2$ |
| Hmt | D-Lys | Phe | Arg | NH$_2$ |
| Mmt | D-Lys | Phe | Arg | NH$_2$ |
| Mmt | D-Orn | Phe | Arg | NH$_2$ |
| Mmt | D-Dab | Phe | Arg | NH$_2$ |
| Mmt | D-Dap | Phe | Arg | NH$_2$ |
| Mmt | D-Arg | Phe | Arg | NH$_2$ |
| Tmt | D-Lys | Phe | Arg | NH$_2$ |
| Tmt | D-Orn | Phe | Arg | NH$_2$ |
| Tmt | D-Dab | Phe | Arg | NH$_2$ |
| Tmt | D-Dap | Phe | Arg | NH$_2$ |
| Tmt | D-Arg | Phe | Arg | NH$_2$ |
| Hmt | D-Lys | Phe | Arg | NH$_2$ |
| Hmt | D-Orn | Phe | Arg | NH$_2$ |
| Hmt | D-Dab | Phe | Arg | NH$_2$ |
| Hmt | D-Dap | Phe | Arg | NH$_2$ |
| Hmt | D-Arg | Phe | Arg | NH$_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin The amino acids of the peptides shown in Tables 5 and 6 may be in either the L- or the D-configuration.

Synthesis of the Peptides

The peptides useful in the methods of the present invention may be chemically synthesized by any of the methods well known in the art. Suitable methods for synthesizing the protein include, for example those described by Stuart and Young in "Solid Phase Peptide Synthesis," Second Edition, Pierce Chemical Company (1984), and in "Solid Phase Peptide Synthesis." *Methods Enzymol.*, 289, Academic Press, Inc, New York (1997).

Methods of Treatment and Prevention of Burn Injury and Secondary Complications

The aromatic-cationic peptides described herein are useful in treating or preventing burn injuries and systemic conditions associated with a burn injury. In some embodiments, the aromatic-cationic peptides may be administered to a subject following a burn and after the onset of detectable symptoms of systemic injury. Thus, the term "treatment" is used herein in its broadest sense and refers to use of an aromatic-cationic peptide for a partial or complete cure of the burn and/or secondary complications, such as organ dysfunction and hypermetabolism.

In other embodiments, the aromatic-cationic peptides of the invention may be administered to a subject following a burn, but before the onset of detectable symptoms of systemic injury in order to protect against or provide prophylaxis for the systemic injury, such as organ damage or hypermetabolism. Thus the term "prevention" is used herein in its broadest sense and refers to a prophylactic use which completely or partially prevents local injury to the skin or systemic injury, such as organ dysfunction or hypermetabolism following burns. It is also contemplated that the compounds may be administered to a subject at risk of receiving burns.

Burns are generally classified accordingly to their seriousness and extent. First degree burns are the mildest and normally only affect the epidermis. The burn site is red, painful, dry, no blisters, very sensitive to touch and the damaged skin may be slightly moist from the leakage of fluid in the deeper layers of the skin. The sensory nerve ends are also exposed and create pain. Mild sunburn is typical of a first degree burn. Second degree burns is where both the epidermis and dermis are affected. The damage is deeper and blisters usually appear on the skin. The skin is still painful and sensitive, as the nerves have been affected as well as the sebaceous glands in the area. Third degree burns are the most serious, as the tissues in all layers of the skin are dead. Normally the damaged area goes down into the subcutaneous tissue. Usually there are no blisters, but the burnt surface can have several types of appearance, from white to black (charred) or bright red from blood in the bottom of the wound. In most cases, it can penetrate down through the superficial fascia, and into the muscle layers where various arteries and veins may be affected. Because the skin nerves are damaged the burn can be quite painless and on touching the skin sometimes it has no sensation whatsoever. The lack of sensation or blanching of the skin blood vessels on pressure indicates damaged skin.

It is contemplated that the invention is applicable to the treatment of burns from any cause, including dry heat or cold burns, scalds, sunburn, electrical burns, chemical agents such as acids and alkalis, including hydrofluoric acid, formic acid, anhydrous ammonia, cement, and phenol, or radiation burns. Burns resulting from exposure to either high or low temperature are within the scope of the invention. The severity and extent of the burn may vary, but secondary organ damage or hypermetabolism will usually arise when the burns are very extensive or very severe (second or third degree burns). The development of secondary organ dysfunction or failure is dependent on the extent of the burn, the response of the patient's immune system and other factors, such as infection and sepsis.

In some embodiments, the aromatic-cationic peptides are used to treat or prevent organ dysfunction secondary to a burn. The chain of physiological processes which lead to organ dysfunction following burns is complex. In subjects with serious burns, release of catecholamines, vasopressin, and angiotensin causes peripheral and splanchnic bed vasoconstriction that can compromise perfusion of organs remote to the injury. Myocardial contractility also may be reduced by the release of TNF-α. Activated neutrophils are sequestered in dermal and distant organs such as the lung within hours following a burn injury, resulting in the release of toxic reactive oxygen species and proteases and producing vascular endothelial cell damage. When the integrity of pulmonary capillary and alveolar epithelia is compromised, plasma and blood leak into the interstitial and intra-alveolar spaces, resulting in pulmonary edema. A decrease in pulmonary function can occur in severely burned patients, as a result of bronchoconstriction caused by humoral factors, such as histamine, serotonin, and thromboxane A2.

Severe burn injury also causes a coagulation necrosis of tissue. This initiates a physiological response in every organ system, the severity of which is related to the extent of the burn. Tissue destruction also results in increased capillary permeability, with profound egress of fluid from the intravascular space to the tissues adjacent to the burn wound. Inordinate amounts of fluid are lost by evaporation from the damaged surface, which is no longer able to retain water. This increase in capillary permeability, coupled with evaporative water loss, causes a hypovolemic shock, which may also in turn contribute to remote organ dysfunction or failure.

Subjects suffering from severe burns are also at great risk of sepsis. Bacterial invasion occurs in a burn patient because the skin no longer acts as a barrier to the entrance of microorganisms. Because of their reduced ability to mount an effective systemic immune response, severely burned patients are susceptible to the development of sepsis and life-threatening septic shock. Sepsis is, however, a separate complication from the organ dysfunction or failure which occurs secondary to burns. Organ dysfunction or failure secondary to burns may occur in the absence of sepsis.

Subjects suffering from a burn injury are also at risk for skeletal muscle dysfunction. While not wishing to be limited by theory, a major cause of the mitochondrial skeletal muscle dysfunction in burns may result from defects in oxidative phosphorylation (OXPHOS) via stimulation of mitochondrial production of reactive oxygen species (ROS) and the resulting damage to the mitochondrial DNA (mtDNA). In some embodiments, the aromatic-cationic peptides induce ATP synthesis via a recovery of the mitochondrial redox status or via the peroxisome proliferator activated receptor-gamma coactivator-1β which is downregulated as early as 6 hours after burn. Thus, the mitochondrial dysfunction caused by burn injury recovers with the administration of the aromatic-cationic peptide.

In one aspect, the methods relate to treating a wound resulting from a burn injury by administering to a subject an effective amount of the aromatic-cationic peptides. The peptides may be administered systemically or topically to the wound. Burn wounds are typically uneven in depth and severity. There are significant areas around the coagulated tissue where injury may be reversible and damage mediated by the inflammatory and immune cells to the microvasculature of the skin could be prevented. In one embodiment, the administration of the peptides will slow or ameliorate the effects of wound contraction. Wound contraction is the process which diminishes the size of a full-thickness open wound, especially a full-thickness burn. The tensions developed during contracture and the formation of subcutaneous fibrous tissue can result in deformity, and in particular to fixed flexure or fixed extension of a joint where the wound involves an area over the joint. Such complications are especially relevant in burn healing. No wound contraction will occur when there is no injury to the tissue; maximum contraction will occur when the burn is full-thickness and no viable tissue remains in the wound. In another embodiment, the administration of the peptides prevent progression of a burn injury from a second degree burn to a third degree burn.

The method for the treatment of burn injury may also be effective for decreasing scarring or the formation of scar tissue attendant the healing process at a burn site. Scarring is the formation of fibrous tissue at sites where normal tissue has been destroyed. The present disclosure thus also includes a method for decreasing scarring specifically at skin tissue areas of second or third degree burn. This method comprises treating an animal with a second or third degree burn with an effective amount of an aromatic cationic peptide.

In a particular embodiment, the aromatic-cationic peptides are administered a subject suffering from a burn in order to treat or prevent damage to distant organs or tissues. In particular, dysfunction or failure of the lung, liver, kidneys, and/or bowel following burns to the skin or other sites of the body has a significant impact on morbidity and mortality. While not wishing to be limited by theory, it is believed that systemic inflammatory responses arise in subjects following burn injury, and that it is this generalized inflammation which leads to remote tissue injury which is expressed as the dysfunction and failure of organs remote from the injury site. Systemic injury, including organ dysfunction and hypermetabolism, is typically associated with second and third degree burns. A characteristic of the systemic injury, i.e., organ dysfunction or hypermetabolism, is that the burn which provokes the subsequent injury or condition does not directly affect the organ in question, i.e., the injury is secondary to the burn.

In one embodiment, the aromatic-cationic peptides are administered to treat or protect damage to liver tissues secondary to a burn. Methods for assessing liver function are well known in the art and include, but are not limited to, using blood tests for serum alanine aminotransferase (ALT) levels, alkaline phosphatase (AP), or bilirubin levels. Methods for assessing deterioration of liver structure are also well known. Such methods include liver imaging (e.g. MRI, ultrasound), or histological evaluation of liver biopsy.

In one embodiment, the aromatic-cationic peptides are administered to treat or protect damage to liver tissues secondary to a burn. Methods for assessing liver function are well known in the art and include, but are not limited to, using blood tests for serum creatinine, or glomerular filtration rate. Methods for assessing deterioration of kidney structure are also well known. Such methods include kidney imaging (e.g., MRI, ultrasound), or histological evaluation of kidney biopsy.

In one embodiment, the aromatic-cationic peptides are administered to prevent or treat hypermetabolism associated with a burn injury. A hypermetabolic state may be associated with hyperglycemia, protein losses, and a significant reduction of lean body mass. Reversal of the hypermetabolic response may be accomplished by administering the aromatic-cationic peptides and by manipulating the subject's physiologic and biochemical environment through the administration of specific nutrients, growth factors, or other agents. As demonstrated in the examples, the present inventors discovered that the aromatic-cationic peptides of the invention may be administered to a subject suffering from a burn in order to treat or prevent hypermetabolism.

In one aspect, the disclosure provides a method for preventing in a subject, a burn injury or a condition associated with a burn injury, by administering to the subject an aromatic-cationic peptide. It is contemplated that the aromatic-cationic peptides may be administered to a subject at risk of receiving burns. In prophylactic applications, pharmaceutical compositions or medicaments of aromatic-cationic peptides are administered to a subject susceptible to, or otherwise at risk of a burn injury to eliminate or reduce the risk, lessen the severity, or delay the outset of the burn injury and its complications.

Another aspect of the disclosure includes methods of treating burn injuries and associated complications in a subject for therapeutic purposes. In therapeutic applications, compositions or medicaments are administered to a subject already suffering from a burn injury in an amount sufficient to cure, or at least partially arrest, the symptoms of the injury, including its complications and intermediate pathological phenotypes in development of the disease. It is contemplated that the aromatic-cationic peptides may be administered to a subject following a burn, but before the development of detectable symptoms of a systemic injury, such as organ dysfunction or failure, and thus the term "treatment" as used herein in its broadest sense and refers to a prophylactic use which completely or partially prevents systemic injury, such as organ dysfunction or failure or hypermetabolism following burns. As such, the disclosure provides methods of treating an individual afflicted with a burn injury.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, preferably a human. When used in vivo for therapy, the aromatic-cationic peptides of the present invention are administered to the subject in effective amounts (i.e., amounts that have desired therapeutic effect). They will normally be administered parenterally, topically, or orally. The dose and dosage regimen will depend upon the degree of burn injury or secondary complications, the characteristics of the particular aromatic-cationic peptide used, e.g., its therapeutic index, the subject, and the subject's history.

The effective amount may be determined during preclinical trials and clinical trials by methods familiar to physicians and clinicians. An effective amount of a peptide, preferably in a pharmaceutical composition, may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g. citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The aromatic-cationic peptides described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water. Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomersal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. In one embodiment, transdermal administration may be performed my iontophoresis.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to other cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For example, dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.1-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. Thereafter, the patient can be administered a prophylactic regime.

In some embodiments, a therapeutically effective amount of an aromatic-cationic peptide may be defined as a concentration of peptide at the target tissue of $10^{-11}$ to $10^{-6}$ molar, e.g., approximately $10^{-7}$ molar. This concentration may be delivered by systemic doses of 0.01 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

In some embodiments, the dosage of the aromatic-cationic peptide is provided at a "low," "mid," or "high" dose level. In one embodiment, the low dose is provided from about 0.001 to about 0.5 mg/kg/h, suitably from about 0.01 to about 0.1 mg/kg/h. In one embodiment, the mid-dose is provided from about 0.1 to about 1.0 mg/kg/h, suitably from about 0.1 to about 0.5 mg/kg/h. In one embodiment, the high dose is provided from about 0.5 to about 10 mg/kg/h, suitably from about 0.5 to about 2 mg/kg/h.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance with the invention can be any mammal, including, for example, farm animals, such as sheep, pigs, cows, and horses; pet animals, such as dogs and cats: laboratory animals, such as rats, mice and rabbits. In a preferred embodiment, the mammal is a human.

EXAMPLES

The present invention is further illustrated by the following examples, which should not be construed as limiting in any way.

Example 1

SS-31 Attenuates the Hypermetabolism After Burn Injury in a Rat Model

Hypermetabolism (HYPM) is a hallmark feature of metabolic disturbance after burn injury. The increased energy expenditure (EE) is associated with accelerated substrate oxidations and shifts of fuel utilization with increased contribution of lipid oxidation to total energy production. Mitochondria are the organelle where the substrate oxidations take place. Mitochondrial dysfunction occurs after burn. It is closely related to the development of HYPM and the altered substrate oxidations. SS-31 (D-Arg-2',6'-dimethyltyrosine-Lys-Phe-$NH_2$) is a tetrapeptide which penetrates into mitochondria, inhibits mitochondrial swelling, and reduces oxidative cell death. This Example tested the SS-31 peptide's potential function on total EE and subsequently, the substrate oxidation after burn injury.

Sprague Dawley rats were randomized into three groups; sham-burn (SB), burn with saline treatment (B) and burn with peptide treatment (BP). Catheters were surgically placed into jugular vein and carotid artery. B and BP animals received 30% total body surface area full thickness burns by immersing the dorsal part into 100° C. water for 12 seconds with immediate fluid resuscitation. BP animals received IV injection of SS-31 (2 mg/kg every 12 h) for three days (FIG. 1). The EE of the animals were constantly monitored for 12 hours in a TSE Indirect Calorimetry System (TSE Co. Germany).

Figure 2:
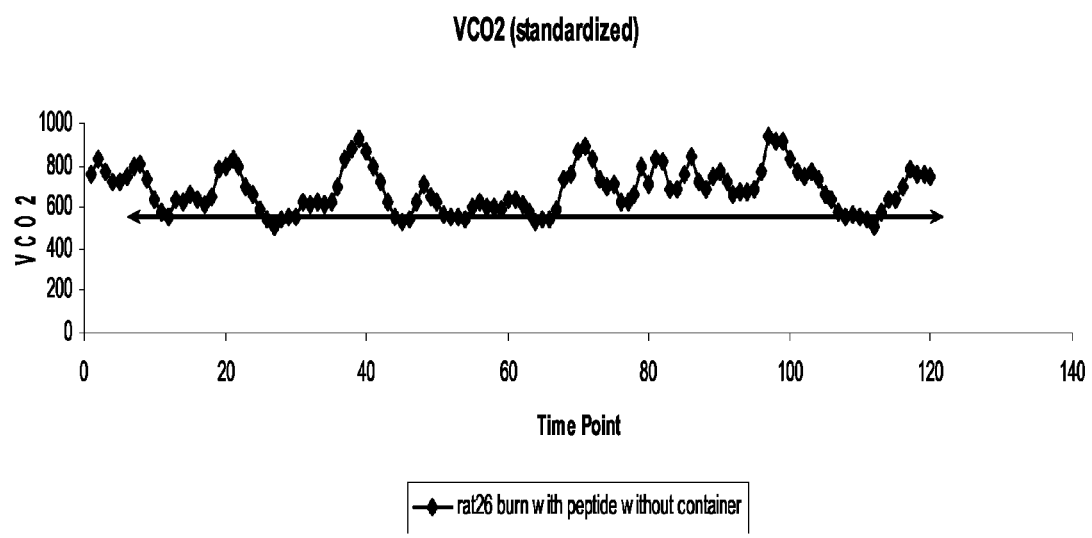
FIG. 2 is a graph showing the $VCO_2$ concentration over time of an exemplary rat that has been burned and administered the SS-31 peptide.

The results of the experiment are shown in Table 7 and FIG. 2. Three days after burn injury, animals in the B group showed significant increases in $VO_2$, $VCO_2$ and EE compared to animals in the SB group. SS-31 treatment significantly reduced $VO_2$, $VCO_2$ and EE (BP versus B $P<0.05$).

TABLE 7

| | Sham (n = 12) | Burn-saline (n = 3) | Burn-SS-31 (2 mg/kg q12h) (n = 3) | P (between burn-saline and burn-SS-31) |
|---|---|---|---|---|
| $VO_2$ (ml/kg/h) | 615 ± 7 | 864 ± 22 | 765 ± 17 | 0.02 |
| $VCO_2$ (ml/kg/h) | 408 ± 6 | 585 ± 15 | 515 ± 16 | 0.03 |
| Energy expenditure (kcal/kg/h) | 3.457 ± 0.062 | 4.927 ± 0.216 | 4.165 ± 0.093 | 0.03 |
| RER | 0.652 ± 0.006 | 0.672 ± 0.002 | 0.669 ± 0.005 | 0.65 |

The results indicate that treatment with SS-31 in rats with a burn injury can attenuate burn-induced HYPM. As such, the aromatic-cationic peptides of the invention are useful in methods of treating burn injuries and secondary complications in subjects in need thereof.

Example 2

SS-31 Protects the Liver from Burn-Induced Apoptosis in the Mouse

Figure 3:
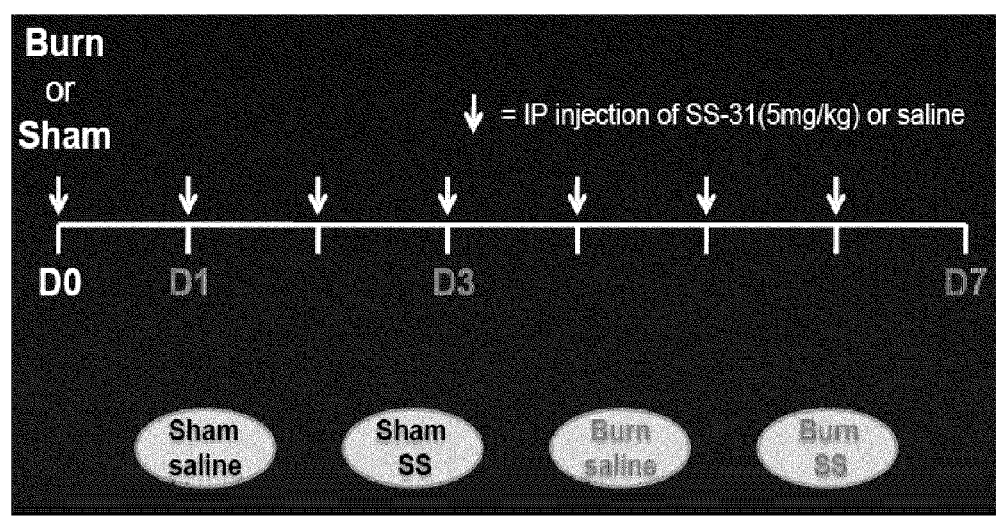
FIG. 3 is a flow chart showing the protocol and dosing schedule for the study presented in Example 2.

Systemic inflammatory response syndrome (SIRS) and multiple organ failure (MOF) are leading causes of morbidity and mortality in severe burn patients. In this Example, the effects of the aromatic-cationic peptides of the invention on liver damage in a mouse model of burn injury were examined. Six to eight week old male C57BL mice were subjected to 30% total body surface area (TBSA) burn injury and subsequently injected daily with saline or SS-31 peptide (5 mg/kg body weight). A weight- and time-matched sham-burn group subjected to lukewarm (~37° C.) water but otherwise treated exactly the same served as controls (FIG. 3). The liver tissues were collected 1, 3, and 7 days after burn injury treatment and used to examine apoptosis by TUNEL method, activated caspase protein levels by Western blots, and caspase activity by an enzymatic reaction assay.

Figure 4:
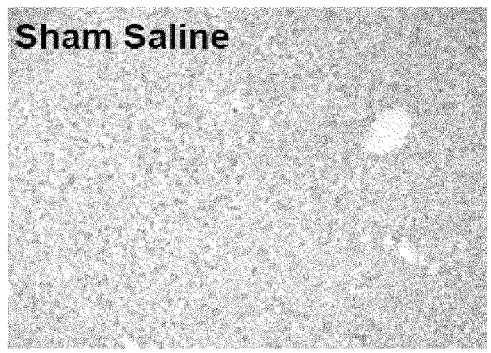
FIG. 4 is a series of micrographs showing sections of liver tissue from the various treatment groups of Example 2.
Figure 4:
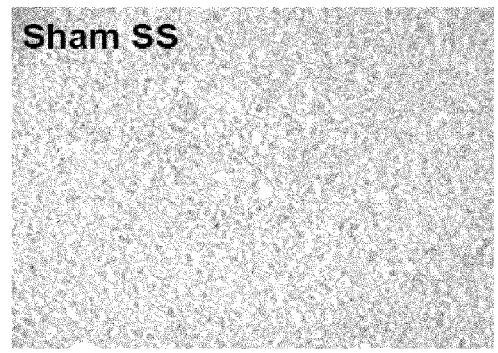
Figure 4:
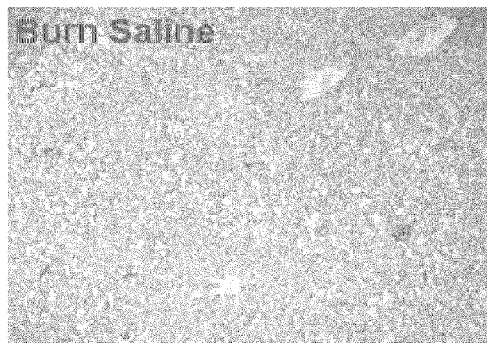
Figure 4:
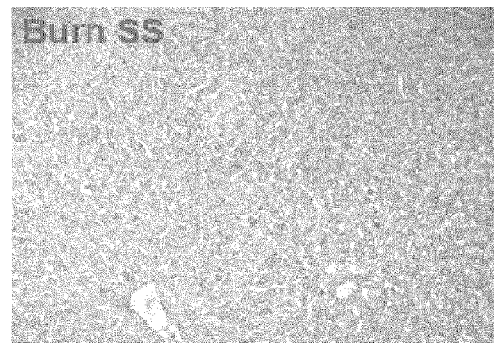
Figure 5:
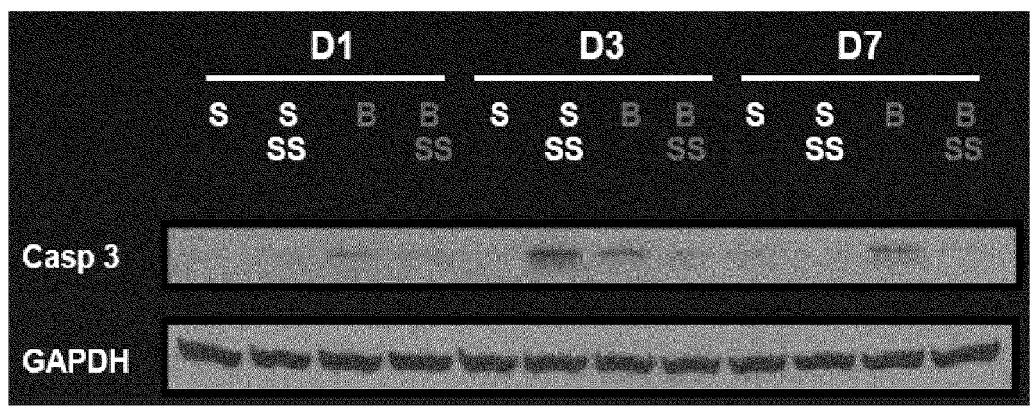
FIG. 5 is photograph of a western blot analysis of caspase-3 cleavage from the various treatment groups of Example 2.
Figure 6:
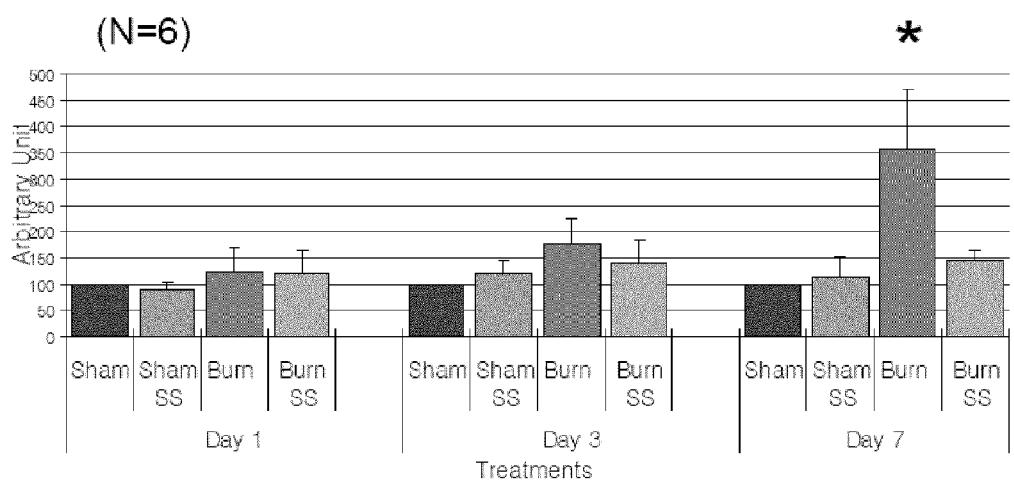
FIG. 6 is a graph showing caspase-3 activity from the various treatment groups of Example 2.
Figure 7:
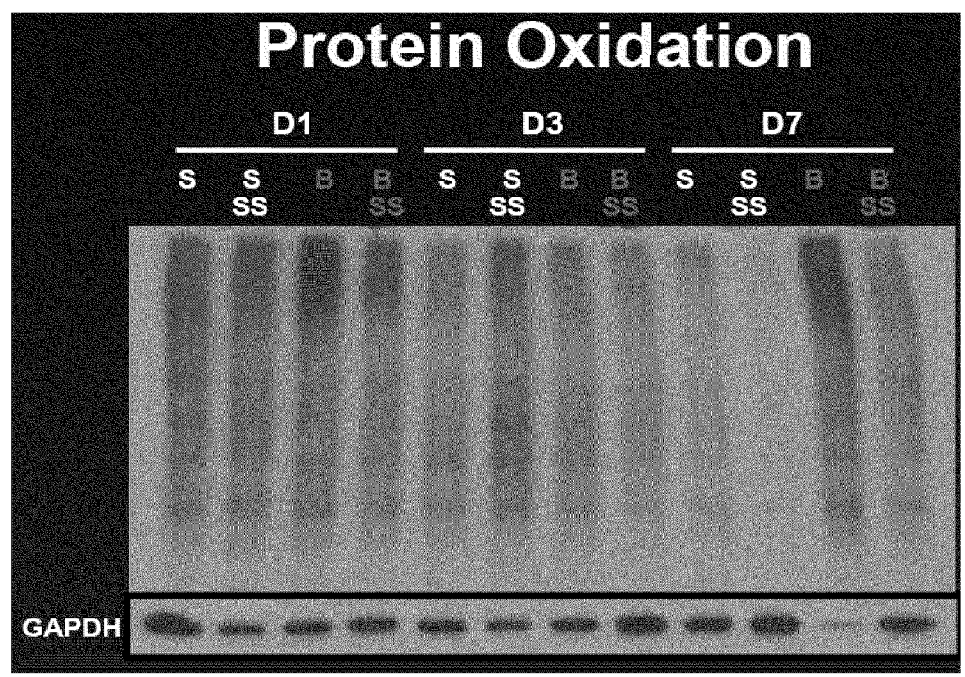
FIG. 7 is a photograph of a western blot analysis showing protein oxidation from the various treatment groups of Example 2.

Burn injury increased the rate of apoptosis in the liver on all days examined, but the most dramatic increase occurred on day 7 post-burn injury. However, treatment with SS-31 peptide minimized the number of cells undergoing apoptosis with its effects most obvious on day 7 of post-burn (FIG. 4). Western blot analysis revealed a progressive increase in the protein levels of activated form of caspase-3 with time following burn injury compared to sham control group (FIG. 5). The SS-31 peptide reversed the increase in the activated form of caspase-3 protein levels on day 3 and 7 post-burn to the levels similar to those of sham control animals. Similar to the changes in the protein levels, the caspase activity increased significantly on post-burn day 7, but the treatment with SS-31 peptide reduced the caspase activity to a level that was statistically not different from that of sham control group (FIG. 6). There was a trend for the increased caspase activity following burn injury to reverse with the SS-31 peptide treatment on day 3 (FIG. 6). There was also decreased protein oxidation following burn injury in mice treated with the SS-31 peptide (FIG. 7).

Thus, this study provides evidence that the SS-31 peptide can reduce burn-induced activation of caspase signaling pathways and subsequently attenuate apoptosis in the liver of mice. As such, the aromatic-cationic peptides of the invention are useful in methods to prevent or treat systemic organ damage, such as liver damage, secondary to a burn.

Example 3

SS-31 Prevents Wound Contraction After Burn Injury

Burn wounds are typically uneven in depth and severity. There are significant areas around the coagulated tissue where injury may be reversible and damage mediated by the inflammatory and immune cells to the microvasculature of the skin could be prevented.

Wound contraction is the process which diminishes the size of a full-thickness open wound, especially a full-thickness burn. The tensions developed during contracture and the formation of subcutaneous fibrous tissue can result in deformity, and in particular to fixed flexure or fixed extension of a joint where the wound involves an area over the joint. Such complications are especially relevant in burn healing. No wound contraction will occur when there is no injury to the tissue, maximum contraction will occur when the burn is full-thickness and no viable tissue remains in the wound. This Example demonstrates the ability of the aromatic-cationic peptides of the invention to reduce or prevent wound contraction.

Figure 8:
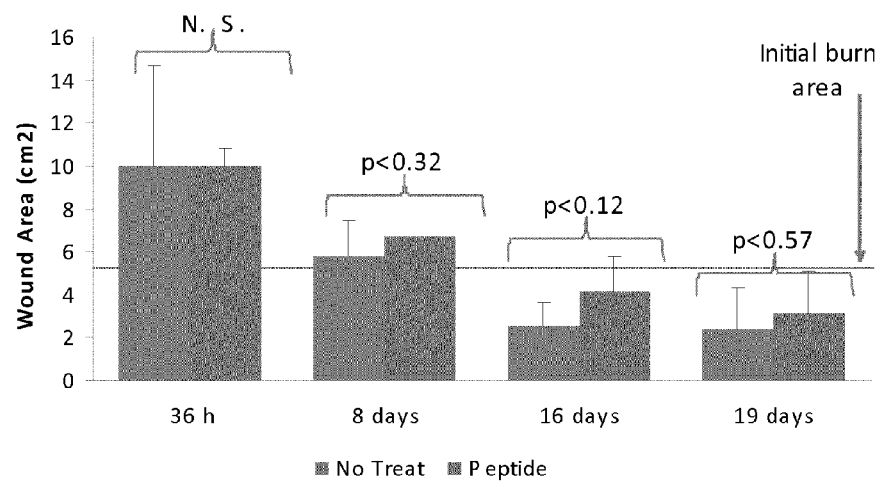
FIG. 8 is a chart showing the wound size comparison between untreated and SS-31 peptide treated groups.

Sprague-Dawley rats (male, 300-350 g) were pre-treated with 1 mg SS-31 peptide administered IP (this corresponds to about 3 mg/kg) one hour prior to burn (65° C. water for 25 sec on the lower back), followed by topical treatment (1 mg on top of the wound), and 1 mg SS-31 peptide administered IP every 12 h for 72 h. Wounds were observed up to ~3 weeks post-burn. In general, the wounds took the appearance of a hard scab, and for the purpose of this experiment, the area of the scab was quantified as a measure of wound size. A slower rate of wound contraction was observed in the peptide-treated group at time points ≥8 days post-burn (p=0.06 by ANOVA) (FIG. 8). Treatment with SS-31 slowed the wound contraction, which indicates the burn injury was less severe compared to burns in animals without the peptide treatment. As such, the aromatic-cationic peptides of the invention are useful in methods of treating wounds associated with a burn injury.

Example 4

SS-31 Alleviates Skeletal Muscle Dysfunction After Burn Injury

To demonstrate the treatment and prevention of post-burn complications, the aromatic-cationic peptides of the invention were tested on a murine model of mammalian burn injury. A major cause of the mitochondrial skeletal muscle dysfunction in burns may result from defects in oxidative phosphorylation (OXPHOS) via stimulation of mitochondrial production of reactive oxygen species (ROS) and the resulting damage to the mitochondrial DNA (mtDNA). This hypothesis is supported by data indicating that the ATP synthesis rate significantly decreases and ROS production increases in skeletal muscle in response to burn injury. This progression underlies the burn pathophysiology, which includes skeletal muscle wasting and cachexia. Thus, this study investigated the potential of aromatic-cationic peptides as a treatment modality to alleviate skeletal muscle dysfunction after burns.

A clinically relevant murine nonlethal local burn injury model was used to address whether aromatic-cationic peptides can prevent/attenuate the adverse effects of burn injury on mitochondrial dysfunction and ER stress. The redox state of the gastrocnemius muscle immediately below a local cutaneous burn (90° for 3 sec) was evaluated by nitroxide EPR. It was found that the redox state in the muscle of burned mice was compromised, with the most dramatic effect at 6 h postburn (P<0.05 compared to day 0 control, n=4), as evidenced by the low rate of nitroxide reduction (FIG. 8).

Next, the effect of SS-31 peptide treatment administered IP 30 min before burn, and immediately after burn (3 mg/kg each dose) was tested. At the 6 h timepoint, peptide treatment significantly increased the rate of nitroxide reduction (lowering the curve of intensity vs. time, FIG. 9). The effect was statistically significant, suggesting that peptide treatment does decrease oxidative stress in muscle underneath the burn. These data indicate that the aromatic-cationic peptides of the invention are useful in methods of preventing or treating secondary complications of a burn injury, such as skeletal muscle dysfunction.

Example 5

SS-31 Treats Burn Wounds and Attenuates Progression of Tissue Damage Following a Burn (Prophetic)

To demonstrate the treatment burn injuries, the aromatic-cationic peptides of the invention are tested on a rat model of mammalian burn injuries. The purpose of these experiments is to determine whether the mitochondrial-directed anti-oxidant peptide SS-31 improves wound healing (i.e. accelerates healing or leads to less scarring) in a partial thickness burn wound. The hypothesis is that SS-31 prevents apoptosis and other deleterious processes, such as oxidative stress, microvascular damage, etc. that lead to expansion of the burn wound (both in depth and area) in the timeframe of 0 to 48 h after the initial injury. Thus, by preventing expansion of the burn wound, it is expected that wound healing will be faster, lead to less scarring, and better appearance after healing. The results shown in Example 3 are consistent with a protective effect of SS-31 in wound healing and suggest that SS-31 can reduce wound contraction in a rat partial thickness burn model. Additional experiments will test whether SS-31 treatment leads to faster healing of burn wounds in a rat model.

First, it is expected that SS-31 will accelerate wound healing in a rat model of burn injury. Sprague Dawley rats will be randomized into three groups; sham-burn (SB), burn with saline treatment (B) and burn with peptide treatment (BP). B and BP animals will receive a 30% total body surface area full thickness burns by immersing the dorsal part into 100° C. water for 12 seconds with immediate fluid resuscitation. BP animals will receive IV injection of SS-31 (2 mg/kg every 12 h) for three days. Wound reepithelialization, contraction, and depth are judged via gross morphology and histologically over a period of 21 days. For this purpose, immediately after wounding, dark marks are applied onto the skin of the animals at the wound edges as well as 1 cm away from the edges. Wounds are digitally photographed over 21 days, and image analysis software used to measure the area of the wound (defined as the scab). In addition, the distances of the marks away from the wound site are used to assess contraction.

At selected time points, wounds will be harvested from the animals. Since the conversion from a second to a third degree wound is expected to occur primarily in the first 48 hours, samples are harvested at 12, 24, and 48 hours. In addition, to monitor the long-term impact on the wound healing process, samples are harvested at 2, 7, 14, and 21 d. The tissues will be fixed and embedded, and sections across the center of the wounds generated for histology and staining with H&E as well as trichrome staining. Slides will be visualized microscopically.

Second, analyses will determine whether or not SS-31 prevents conversion of a partial thickness burn to a full-thickness burn. For this purpose, TUNEL staining and caspase-3 assays are carried out to see if apoptosis occurs in the hair follicles of the skin. Skin samples obtained from time points between 0 and 48 h are used for this purpose. Normal skin is used as a "blank" sample. TUNEL assays are performed using commercial kits according to the manufacturer's procedures. Active caspase-3 is detected on the slides by immunofluorescence using a rabbit anti-active caspase-3 antibody. Quantification of TUNEL and caspase-3 positivity is done on digitally acquired images at high power. The number of positive cells per high power field is determined, and compared among the groups.

Third, luminescence mapping is performed using Doppler imaging to assess wound blood flow. Two hours after burn, the dorsum of the animal is imaged on a scanning laser Doppler apparatus to quantify the superficial blood flow distribution in the skin within and outside of the burn area. For luminescence mapping, 100 male Sprague-Dawley rats are used. Eighty animals receive a large (covering 30% of the total body surface area) full-thickness burn injury on the dorsum. This is a well-established model. They are divided into 2 groups, one treated with SS-31 and the other with placebo (saline) treatment. Each group is further divided into 4 subgroups consisting of 4 time points where animals will be sacrificed for further analysis. Prior to sacrifice, luminescence imaging is carried out, followed by euthanasia and skin tissue sampling for subsequent histology. The remaining 20 animals will receive a "sham burn" and will be treated with SS-31 or saline. Euthanasia is performed on two animals in each of the corresponding 4 time points. On average, each animal will be housed for 10 days (including the pre-burn days in the animal farm) in separate cages.

It is predicted that SS-31 administration will accelerate wound healing and attenuate the progression of burn injuries that normally develops in the rat model. Measured outcomes include wound contraction, reepithelialization distance, us well as any other features that may be of interest in the dermis, such as cellularity and collagen organization. Ki67 proliferation antigen will be assessed, as well as TUNEL and caspase-3 positivity. Blood flow (as measured by luminescence mapping) will also be measured. A comparison is made between control rats and burned rats administered SS-31. Successful treatment of burn injuries by the aromatic-cationic peptides of the invention is indicated by a reduction in one or more of the markers associated with burn injury progression enumerated above.

Example 6

SS-31 Protects Against Protects Against Sunburn and Attenuates Progression of Tissue Damage Following a Sunburn (Prophetic)

In this Example, the effects of aromatic-cationic peptides to protect against sunburn injury in a mammalian model are examined. Hairless mice, with skin characteristics similar to humans, are exposed to excessive UV radiation over the course of a week. Subjects are randomly divided into three groups: (i) burn-saline, (ii) burn-SS-31 (4 mg·kg$^{-1}$·day$^{-1}$; low dose group), (ii) burn-SS-31 (40 mg·kg$^{-1}$·day$^{-1}$; high dose group). Peptide dissolved in 1 ml/kg saline will be administered intravenously twice a day for seven days.

It is predicted that SS-31 administration will accelerate wound healing and attenuate the progression of sunburn injuries that normally develops in the model. Measured outcomes include wound contraction, reepithelialization distance, as well as any other features that may be of interest in the dermis, such as cellularity and collagen organization. Ki67 proliferation antigen will be assessed, as well as TUNEL and caspase-3 positivity. Blood flow (as measured by luminescence mapping) will also be measured. A comparison is made between control rats and burned rats administered SS-31. Controls include sham-burn (SB) and burn with saline treatment (B). Successful prevention or amelioration of sunburn injuries by the aromatic-cationic peptides of the invention is indicated by a reduction in one or more of the markers associated with burn injury progression enumerated above.

Example 7

SS-31 Attenuates the Burn Induced Hypermetabolism by the Down Regulation of UCP-1 Expression in Brown Adipose Tissue Hypermetabolism is the hallmark feature of metabolic disturbance after burn injury. Mitochondria dysfunction occurs after burns, and is closely related to the development of hypermetabolism (and altered substrate oxidation). It was shown that mitochondria targeted small peptide, SS-31, which penetrates into mitochondria, inhibits mitochondrial swelling, and reduces oxidative cell death, attenuates the hypermetabolism after burn injury. Uncoupling protein 1 (UCP-1) is specifically expressed in the brown adipose tissue, and plays a key role in producing heat. The purpose of this example is to elucidate that the down-regulation of UCP-1 is the key mechanism to attenuate the hypermetabolism in burns treated with SS-31.

Methods. Sprague Dawley rats were randomly divided into 5 groups; sham (S), sham with saline treatment (SSal), sham with SS-31 treatment (SPep), burn with saline treatment (BSal) and burn with SS-31 treatment (BPep). In burn group, the back of animal was immersed into 100° C. water for 12 seconds to produce III degree 30% TBSA burns under general anesthesia. Sham burn was produced by immersing the lukewarm water in the same manner. Both groups of animals received 40 ml/kg intraperitoneal saline injection for the resuscitation following the injury. A venous catheter was placed surgically into the right jugular vein subsequent to sham or burn injury. SS-31 (2 mg/kg) or saline was injected as priming, and infused for 7 days (4 mg/kg/day) using osmotic pump (Durect, CA). S group meant the control group, which did not receive any general anesthesia, sham or burn injury and catheter placement. The indirect calorimetry was performed for 24 hours at 6 days after burn injury in a TSE Indirect Calorimetry System (TSE Co. Germany), and VO2, VCO$_2$ and energy expenditure were recorded every six minutes. Interscapullar brown adipose tissue was collected after the indirect calorimetry, and UCP-1 expression in the brown adipose tissue was evaluated by Western blot.

Results. VO$_2$, VCO$_2$ and energy expenditure were significantly increased in BSal group compared to SSal group (p=0.000, p=0.000 and p=0.000, respectively). Those in BPep group were significantly attenuated compared to BSal group (p<0.01, p<0.05 and p<0.05, respectively). UCP-1 expression in BSal group was 1.5 times higher than in SSal group (p<0.05). Meanwhile, that in BPep group was 32% decreased compared to BSal group (p=0.057).

These results show that SS-31 attenuates the burn induced hypermetabolism by the down regulation of UCP-1 expression in brown adipose tissue. As such, the aromatic cationic peptides described herein are useful in methods for treating a subject suffering from a burn injury.

Example 8

SS-31 Induces ATP Synthesis Rate Following a Burn in a Mouse Burn Model

To demonstrate the treatment and prevention of post-burn complications, the aromatic-cationic peptides of the invention were tested on a murine model of mammalian burn injury. A major cause of the mitochondrial skeletal muscle dysfunction in burns may result from defects in oxidative phosphorylation (OXPHOS) via stimulation of mitochondrial production of reactive oxygen species (ROS) and the resulting damage to the mitochondrial DNA (mtDNA). This hypothesis is supported by data indicating that the ATP synthesis rate significantly decreases and ROS production increases in skeletal muscle in response to burn injury. This progression underlies the burn pathophysiology, which includes skeletal muscle wasting and cachexia. Thus, this study investigated the potential of aromatic-cationic peptides as a treatment modality to alleviate skeletal muscle dysfunction after burns.

This example evaluated the effects of an aromatic cationic peptide SS-31 in a clinically relevant burn trauma model using $^{31}$P NMR and electron paramagnetic resonance (EPR) in vivo. The results showed that SS-31 peptide induces ATP synthesis rate by causing recovery of the mitochondrial redox status at 6 hours after burn.

Materials and Methods. Male 6-week-old CD1 mice weighing 20-25 g were anesthetized by intraperitoneal (i.p.) injection of 40 mg/kg pentobarbital sodium. The left hind limb of all mice in all groups was shaved. Each burned mouse was subjected to a nonlethal scald injury of 3-5% total body surface area (TBSA) by immersing its left hind limb in 90° C. water for 3 sec.

NMR spectroscopy is described in detail in Padfield, et al., *Proc Natl Acad Sci USA* 102: 5368-5373 (2005). Briefly, mice were randomized into burn, burn+SS-31 peptide, control, and control+peptide groups. The SS-31 peptide (3 mg/kg) was injected intraperitoneally at 30 min prior to burn and a second injection immediately after the burn. NMR experiments were performed in a horizontal bore magnet (proton frequency 400 MHz, 21 cm diameter, Magnex Scientific) using a Bruker Avance console. A 90° pulse was optimized for detection of phosphorus spectra (repetition time 2 s, 400 averages, 4K data points). Saturation 90°-selective pulse trains (duration 36.534 ms, bandwidth 75 Hz) followed by crushing gradients were used to saturate the γ-ATP peak. The same saturation pulse train was also applied downfield of the inorganic phosphate (Pi) resonance, symmetrically to the γ-ATP resonance. T$_1$ relaxation times of Pi and phosphocreatine (PCr) were measured using an inversion recovery pulse sequence in the presence of γ-ATP saturation. An adiabatic pulse (400 scans, sweep with 10 KHz, 4K data) was used to invert Pi and PCr, with an inversion time between 152 ms and 7651 ms.

EPR spectroscopy is described in detail in Khan et al. "Burn Trauma in skeletal muscle results in oxidative stress as assessed by in vivo electron paramagnetic resonance." *Mol Med Reports* 1: 813-819 (2008). Briefly, mice were randomized into burn, burn+SS-31 peptide and control groups. The SS-31 peptide (3 mg/kg) was injected intraperitoneally at 0, 3, 6, 24, and 48 hours post-burn. EPR measurements were carried out with a 1.2-GHz EPR spectrometer equipped with a microwave bridge and external loop resonator specially designed for in vive experiments. The optimal spectrometer parameters were: incident microwave power, 10 mW; magnetic field center, 400 gauss; modulation frequency, 27 kHz. The decay kinetics of intravenously-injected nitroxide (150 mg/kg) were measured at the various time points, which indicated the mitochondrial redox status of the muscle.

Figure 9:
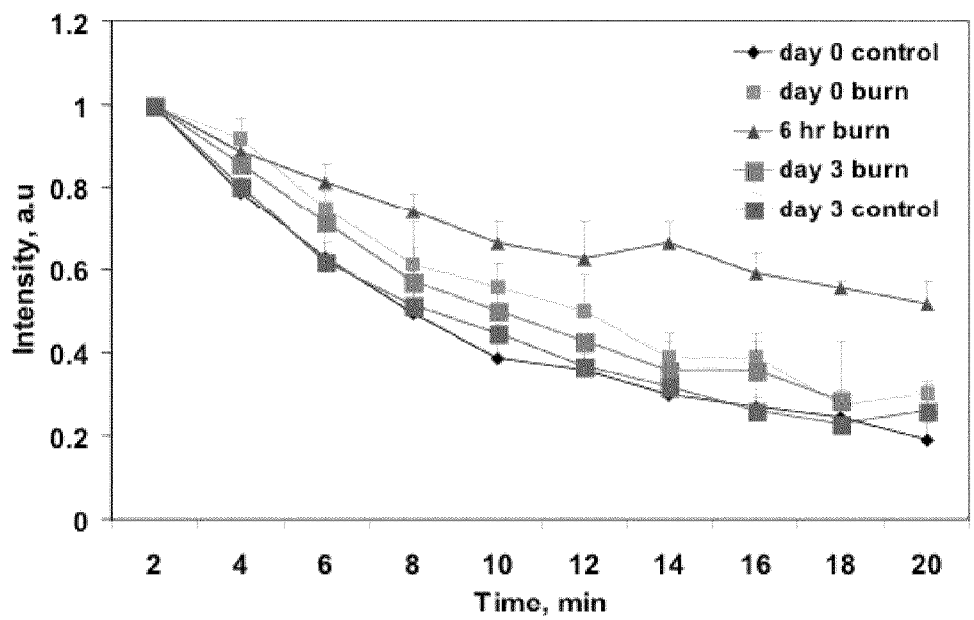
FIG. 9 is a graph showing the reduction of the nitroxide in the gastrocnemius muscle before and after a burn injury.
Figure 10:
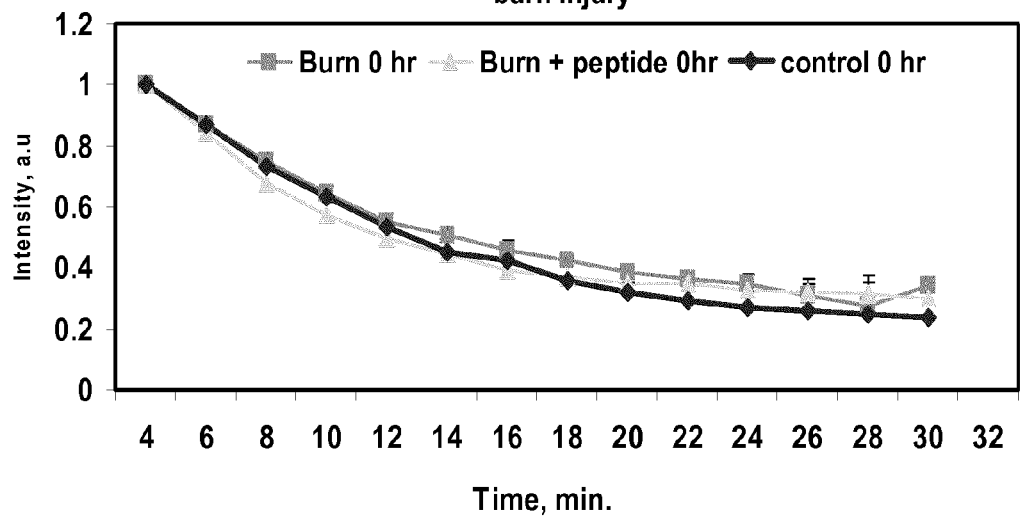
FIG. 10 is a graph showing the reduction in nitroxide in the gastrocnemius at 0 h after a burn injury in subjects administered saline or SS-31 peptide.
Figure 15:
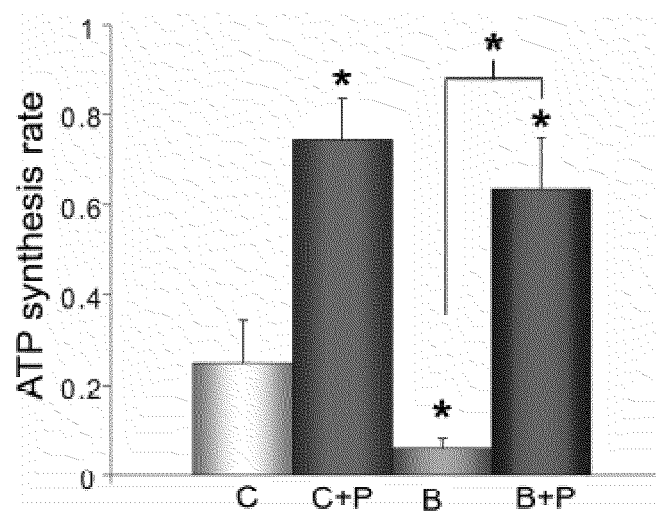
FIG. 15 is a graph of ATP synthesis rate (μmol/g/s) in control (C), control+SS-31 peptide (C+P), burned (B), and burned+peptide SS-31 (B+P) as measured by $^{31}P$ NMR at 6 hours after burn.

Results. EPR was used to measure the redox status of burn and burn+peptide groups at various times after the burn. FIG. 9 is a graph showing the reduction of the nitroxide in the gastrocnemius muscle before and after a burn injury. These results show that subjects experience a significantly elevated redox status at 6 h after a burn injury. FIGS. 10-14 show the reduction in nitroxide in the gastrocnemius muscle before and after a burn injury in control, burn and burn+peptide groups at 0, 3, 6, 24, and 48 h after a burn injury, respectively. According to EPR, a significant decrease in redox status of burn and burn+peptide groups as compared to control was detected (p<0.05) at 6 h after burn; also, significant increase (recovery) in redox status of burn+peptide group as compared to burn was detected (p<0.05) (FIG. 15).

Figure 11:
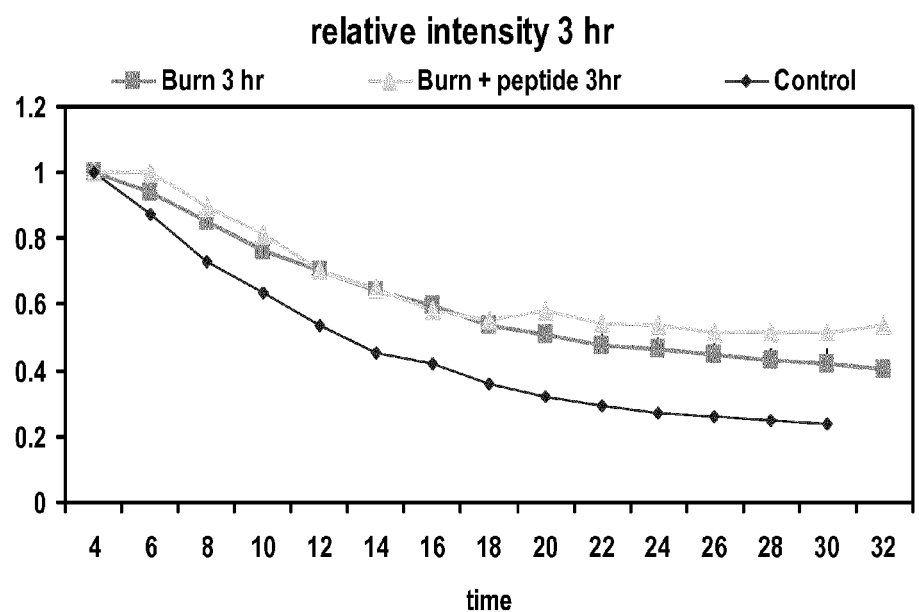
FIG. 11 is a graph showing the reduction in nitroxide in the gastrocnemius at 3 h after a burn injury in subjects administered saline or SS-31 peptide.

Burn injury caused significant reduction of ATP synthesis rate at 6 hours (FIG. 11, Table 1). The peptide SS-31 induced a significant increase in the ATP synthesis rate in burned mice and a non-statistically significant increase in controls.

TABLE 8

Results of in vivo $^{31}$P-NMR saturation transfer experiments.

|  | Healthy Controls (n = 5) | Controls + Peptide (n = 5) | Burn (n = 8) | Burn + Peptide (n = 8) |
|---|---|---|---|---|
| $\Delta M/M_0$ | 0.24 ± 0.05 | 0.185 ± 0.02 (P = 0.097) | 0.23 ± 0.05 (P = 0.902) | 0.31 ± 0.06 (P = 0.488) |
| $T_{1obs}$ (s) | 1.16 ± 0.14 | 1.16 ± 0.14 | 1.33 ± 0.27 | 1.33 ± 0.27 |
| $P_i$ (μmol/g) | 1.01 ± 0.28 | 5.49 ± 0.28 (P = 0.0008) | 0.34 ± 0.25 (P = 0.006) | 2.93 ± 0.56 (P = 0.035) |
| ATP synthesis rate (μmol/g/s) | 0.25 ± 0.09 | 0.74 ± 0.09 (P = 0.008) | 0.06 ± 0.02 (P = 0.026) | 0.63 ± 0.11 (P = 0.046) |

Figure 12:
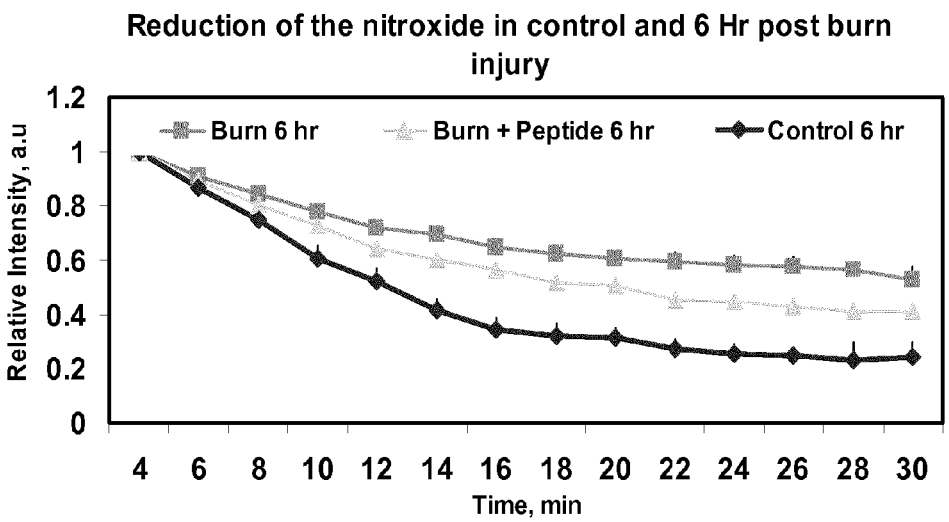
FIG. 12 is a graph showing the reduction in nitroxide in the gastrocnemius at 6 h after a burn injury in subjects administered saline or SS-31 peptide.
Figure 13:
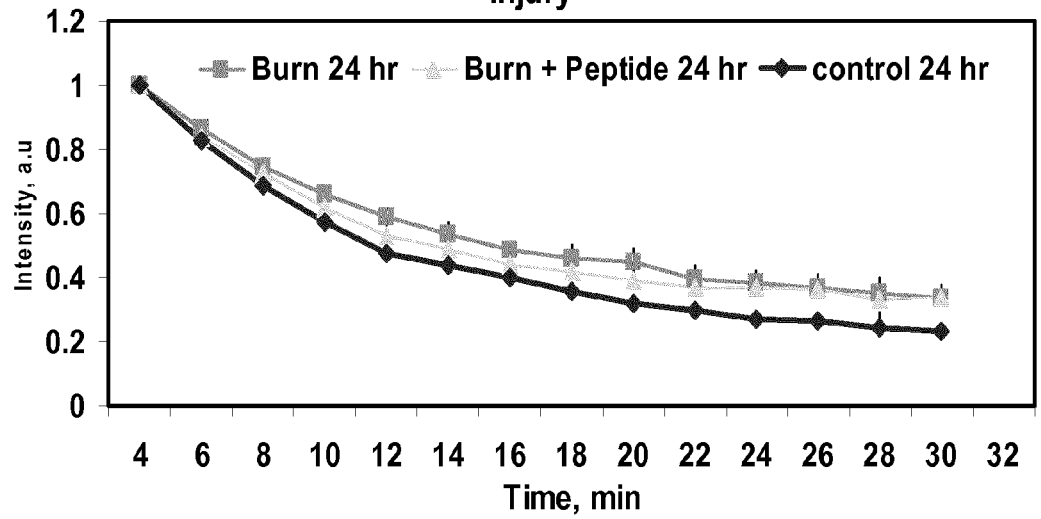
FIG. 13 is a graph showing the reduction in nitroxide in the gastrocnemius at 24 h after a burn injury in subjects administered saline or SS-31 peptide.
Figure 14:
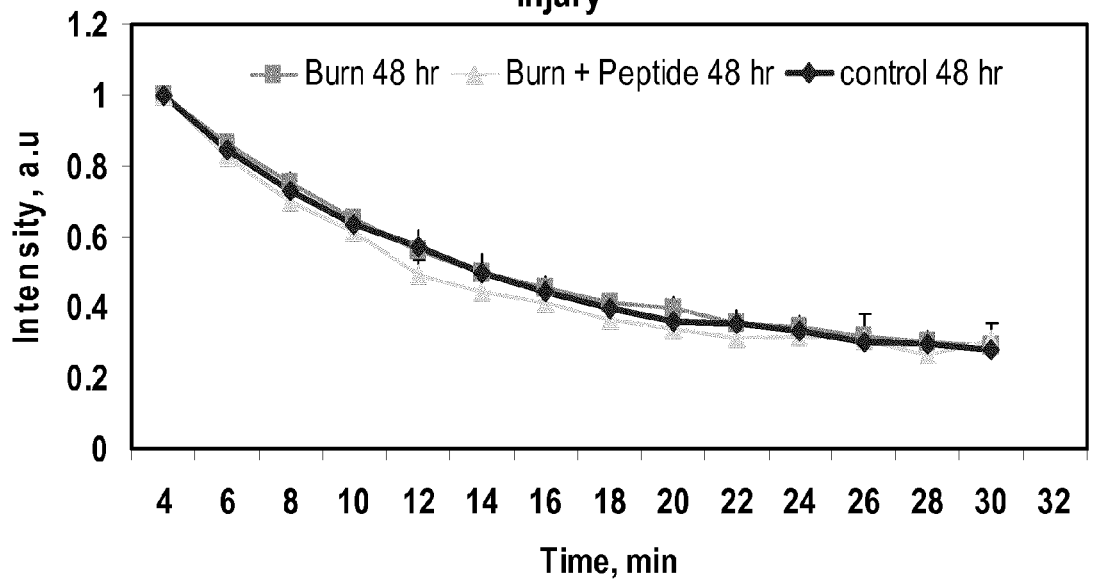
FIG. 14 is a graph showing the reduction in nitroxide in the gastrocnemius at 48 h after a burn injury in subjects administered saline or SS-31 peptide.

As shown in Table 8 and illustrated in FIG. 15: ATP synthesis rate (Pi→γATP) at 6 hours after burn was significantly reduced in burned (B) mice; and SS-31 treatment resulted in significantly increased ATP synthesis rate in both control (C+P) and burned (B+P) mice. Importantly, ATP synthesis rate was significantly increased in burned mice injected with the SS-31 (B+P), as compared to burned alone mice (B) (P=−0.0001). Moreover, when the ATP synthesis rate (reaction PCr→γATP) was compared in burned mice and mice injected with SS-31 the increase was statistically significant (P=0.006) (Table 9). According to EPR, a significant decrease in the redox status of burn and burn+SS-31 groups as compared to control was detected (p<0.05); also, a significant increase (recovery) in the redox status of burn+peptide group as compared to burn alone was observed (p<0.05), (FIG. 12).

TABLE 9

Results of in vivo $^{31}$P-NMR saturation transfer experiments performed on the hindlimb skeletal muscle of mice ATP synthesis rate (reaction PCr → γATP)

|  | Healthy Controls (n = 5) | Controls + Peptide (n = 5) | Burn (n = 8) | Burn + Peptide (n = 8) |
|---|---|---|---|---|
| $\Delta M/M_0$ | 0.24 ± 0.05 | 0.15 ± 0.02 (P = 0.097) | 0.23 ± 0.05 (P = 0.902) | 0.31 ± 0.06 (P = 0.488) |
| $T_{1obs}$ (s) | 1.16 ± 0.14 | 1.16 ± 0.14 | 1.33 ± 0.27 | 1.33 ± 0.27 |
| $K_f$ (s$^{-1}$) | 0.21 ± 0.04 | 0.14 ± 0.02 (P = 0.096) | 0.17 ± 0.04 (P = 0.605) | 0.24 ± 0.05 (P = 0.771) |
| PCr (μmol/g) | 2.28 ± 0.23 | 3.76 ± 0.51 (P = 0.047) | 1.16 ± 0.23 (P = 0.01) | 3.25 ± 0.29 (P = 0.054) |
| ATP synthesis rate (μmol/g/s) | 0.50 ± 0.12 | 0.50 ± 0.06 (P = 0.96) | 0.24 ± 0.01 (P = 0.007) | 0.72 ± 0.11 (P = 0.119) |

In summary, the results show that SS-31 induces ATP synthesis rate possibly via a recovery of the mitochondrial redox status or via the peroxisome proliferator activated receptor-gamma coactivator-1β (PGC-1β) which is down-regulated as early as 6 hours after burn. See Tzika et al., *Int J Mol Med* 21: 201-208, 2008. Thus, the mitochondrial dysfunction caused by burn injury recovers with the administration of the SS-31 peptide. Administration of the SS-31 peptide increased ATP synthesis rate substantially even in control healthy mice. These data indicate that the aromatic-cationic peptides of the invention are useful in methods of preventing or treating secondary complications of a burn injury, such as skeletal muscle dysfunction.

Example 9

SS-31 Effects on Mitochondrial Aconitase Activity

Mitochondrial aconitase is part of the TCA cycle and its activity has been directly correlated with the TCA flux. Moreover, its activity is inhibited by ROS and thus it is considered as an index of oxidative stress. Here we present the local and systematic effects of burn on the mitochondrial aconitase activity using a 5% TBSA mice burn model. The effects of a mitochondrial peptide (SS-31) had been also examined.

Figure 16:
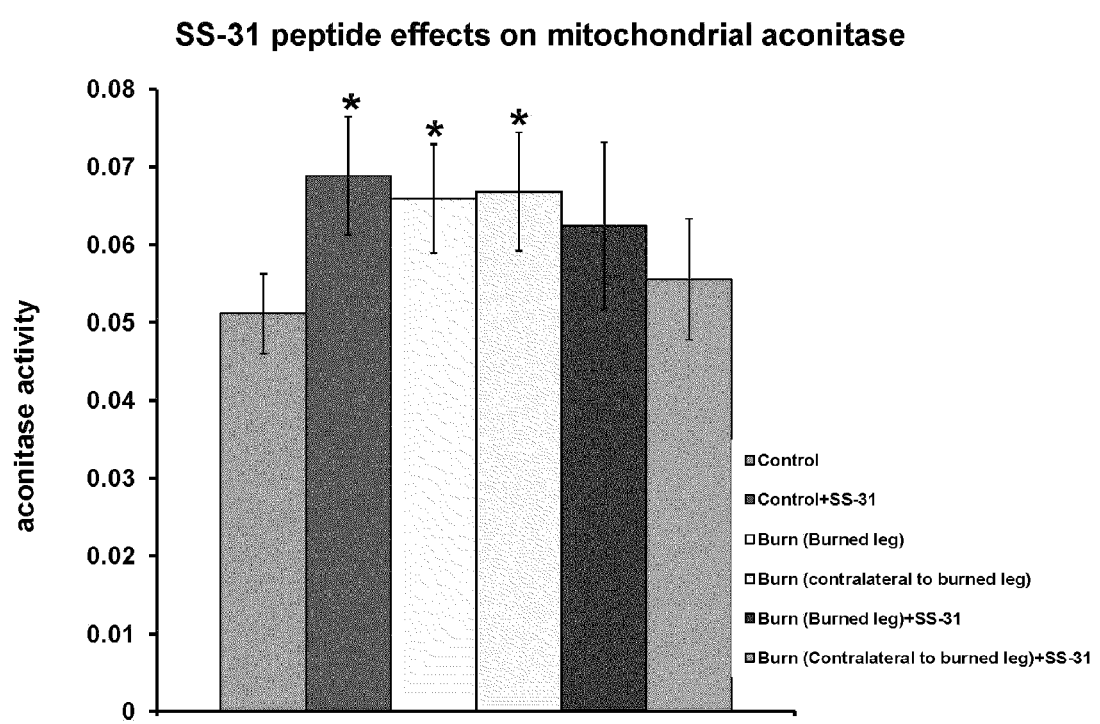
FIG. 16 is a graph of mitochondrial aconitase activity in control, burn, and peptide-treated subjects.

Although in burn, we would expect decreased levels of mitochondrial aconitase activity due to the increased ROS production, in our study we observed increased mitochondrial aconitase activity both in burned (local burn effect) and contralateral to burned leg (systemic burn effect), most probably due to the hypermetabolism that burn injury induces (FIG. 16). Thus, the increased ROS production known to occur in burn injury and could inhibit this mitochondrial aconitase activity cannot overcome the also existing hypermetabolism in burn, in terms of mitochondrial aconitase activity and thus TCA flux. A similar observation has been also shown in the case of excersise/repeated contractions in intact human and isolated mouse skeletal muscle although an increase in ROS is also observed in this situation. Given the decreased ATP synthesis rate, we also observed in skeletal muscle from the same burn model, this result could account as an indirect evident that in this particular hypermetabolic syndrome TCA is futile.

These results show that SS-31 administration in burned animals decreased mitochondrial aconitase activity up to the control levels, indicating thus that SS-31 recovers the TCA flux, maybe in response to a more effective aerobic respiration as this is suggested by the increased ATP synthesis rate compared with untreated burned animals.

Example 10

A Single Dose of SS-31 Induces ATP Synthesis Rate Following a Burn in a Mouse Burn Model This example evaluated the effects of an aromatic cationic peptide SS-31 in a clinically relevant burn trauma model using $^{31}P$ NMR in vivo. The results showed that SS-31 peptide induces ATP synthesis rate by causing recovery of the mitochondrial redox status after burn.

Male 6-week-old CD1 mice (20-25 g) were anesthetized by intraperitoneal injection of 40 mg/kg pentobarbital sodium and the left hind limb of all mice was shaved. Burn injury was inflicted by a nonlethal scald injury of 3-5% total body surface area by immersing the left hind limb in 90° C. water for 3 sec. Mice were randomized into burn (B), burn+SS-31 (B+P), control (C) and control+SS-31 (C+P) groups. SS-31 (3 mg/kg) was injected intaperitoneally at 30 min before burn and immediately after burn. A separate group of burned animals received only one dose of the SS-31 peptide immediately after burn.

TABLE 10

Results of in vivo $^{31}$P-NMR saturation transfer experiments.

| | Healthy Controls (n = 5) | Controls + Peptide (n = 5) | Burn (n = 8) | Burn + Peptide (n = 8) | Burn + Peptide* (n = 8) |
|---|---|---|---|---|---|
| $\Delta M/M_0$ | 0.24 ± 0.05 | 0.15 ± 0.02 (P = 0.097) | 0.23 ± 0.05 (P = 0.902) | 0.31 ± 0.06 (P = 0.488) | 0.39 ± 0.07 (P = 0.072) |
| $T1_{obs}$ (s) | 1.16 ± 0.14 | 1.16 ± 0.14 | 1.33 ± 0.27 | 1.33 ± 0.27 | 1.33 ± 0.27 |
| Pi (µmol/g) | 1.01 ± 0.28 | 5.49 ± 0.28 (P = 0.0008) | 0.34 ± 0.25 (P = 0.006) | 2.93 ± 0.56 (P = 0.035) | 1.41 ± 0.26 (P = 0.166) |
| ATP synthesis rate (µmol/g/s) | 0.25 ± 0.09 | 0.74 ± 0.09 (P = 0.008) | 0.06 ± 0.02 (P = 0.026) | 0.63 ± 0.11 (P = 0.046) | 0.36 ± 0.08 (P = 0.211) |

The results are shown in Table 10. Values are means±SE; $\Delta M/M0$ is the fractional change in Pi magnetization as a result of saturation transfer; $T1_{obs}$ is the observed spin lattice relaxation time of Pi during γATP saturation in seconds; ATP synthesis is calculated as [Pi]×k; [Pi] is the concentration of Pi extrapolated from the baseline NMR spectrum, comparing Pi and γATP peaks and ATP concentration measured with bioluminescence assay; k is calculated as $(1/T1_{obs})\times(\Delta M/M0)$; P-values (unpaired Student's t-test) are for comparisons between experimental and control groups; * indicates only one dose of SS-31 peptide (3 mg/kg) was injected to animals immediately after burn. Thus, the last column of the table shows that SS-31 normalizes ATP synthesis rate even at a single dose after burn. These data indicate that the aromatic-cationic peptides of the invention are useful in methods of preventing or treating secondary complications of a burn injury.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and compositions within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All references cited herein are incorporated herein by reference in their entireties and for all purposes to the same extent as if each individual publication, patent, or patent application was specifically and individually incorporated by reference in its entirety for all purposes.

Other embodiments are set forth within the following claims.

What is claimed is:

1. A method for treating wound contraction in a burned tissue in a subject in need thereof, comprising administering to the subject an effective amount of a peptide having the formula D-Arg-2',6'-dimethyltyrosine-Lys-Phe-NH$_2$.

2. The method of claim 1, wherein the wound contraction comprises the formation of subcutaneous fibrous tissue.

3. The method of claim 1, wherein the treatment comprises reducing or preventing the formation of subcutaneous fibrous tissue.

4. The method of claim 1, wherein the treatment comprises reducing or preventing fixed flexure or fixed extension of a joint.

5. The method of claim 1, wherein the peptide is administered intravenously, orally, subcutaneously, transdermally, intraperitoneally, or topically.

6. The method of claim 5, wherein the peptide is administered topically.

7. The method of claim 1, wherein the burned tissue is a sunburn or a radiation burn.

8. The method of claim 1, wherein the peptide is administered during or after the onset of wound contraction.

9. The method of claim 1, wherein the peptide is administered at a dosage of about 3 mg/kg body weight.

* * * * *